(12) United States Patent
Kajiyama et al.

(10) Patent No.: US 6,428,749 B1
(45) Date of Patent: Aug. 6, 2002

(54) ADVANCED THERMAL GRADIENT DNA CHIP (ATGC), THE SUBSTRATE FOR ATGC, METHOD FOR MANUFACTURING FOR ATGC, METHOD AND APPARATUS FOR BIOCHEMICAL REACTION, AND STORAGE MEDIUM

(75) Inventors: Tomoharu Kajiyama, Kokubunji; Yuji Miyahara; Katsuji Murakawa, both of Kodaira, all of (JP)

(73) Assignee: Hitachi, Ltd., Tokyo (JP)

(*) Notice: Subject to any disclaimer, the term of this patent is extended or adjusted under 35 U.S.C. 154(b) by 0 days.

(21) Appl. No.: 09/527,233

(22) Filed: Mar. 16, 2000

(30) Foreign Application Priority Data

Dec. 15, 1999 (JP) ............................................ 11-356433

(51) Int. Cl.[7] .......................... G01N 15/00; G01N 1/00; G01N 33/53; C12Q 1/68
(52) U.S. Cl. ............................ 422/68.1; 422/50; 435/6; 435/7.1
(58) Field of Search ........................... 422/68.1; 435/6, 435/7.1

(56) References Cited

U.S. PATENT DOCUMENTS 4,246,044 A * 1/1981 Yanase ........................ 148/1.5
6,093,370 A * 7/2000 Yasuda et al. ............. 422/68.1

FOREIGN PATENT DOCUMENTS

JP    11-127900    5/1999

OTHER PUBLICATIONS

Schena et al., Science, vol. 270, pp. 467–470 (1990).

Khrapko et al. JDNA Sequencing and Mapping, vol. 1, pp. 375–388 (1991).

K. J. Breslauer, R. Frank, H. Blocker and L.A. Marky, "Predicting DNA Duplex Stability from the Base Sequence," Proc. Natl, Acad. Sci. USA (Jun. 1986) vol. 83, pp. 3746–3750.

* cited by examiner

Primary Examiner—Ardin H. Marschel

(57) ABSTRACT

A biochemical reaction detection chip capable of controlling the temperature for biochemical reactions including hybridizations and its substrate. The function of the chip is performed by comprising a plurality of islands of a heat conducting material on the membrane of the substrate, the islands being spaced from each other and individually provided with temperature controllers, and the probes immobilized on the substrate.

14 Claims, 17 Drawing Sheets

A CROSS SECTION VIEW AT A-A'

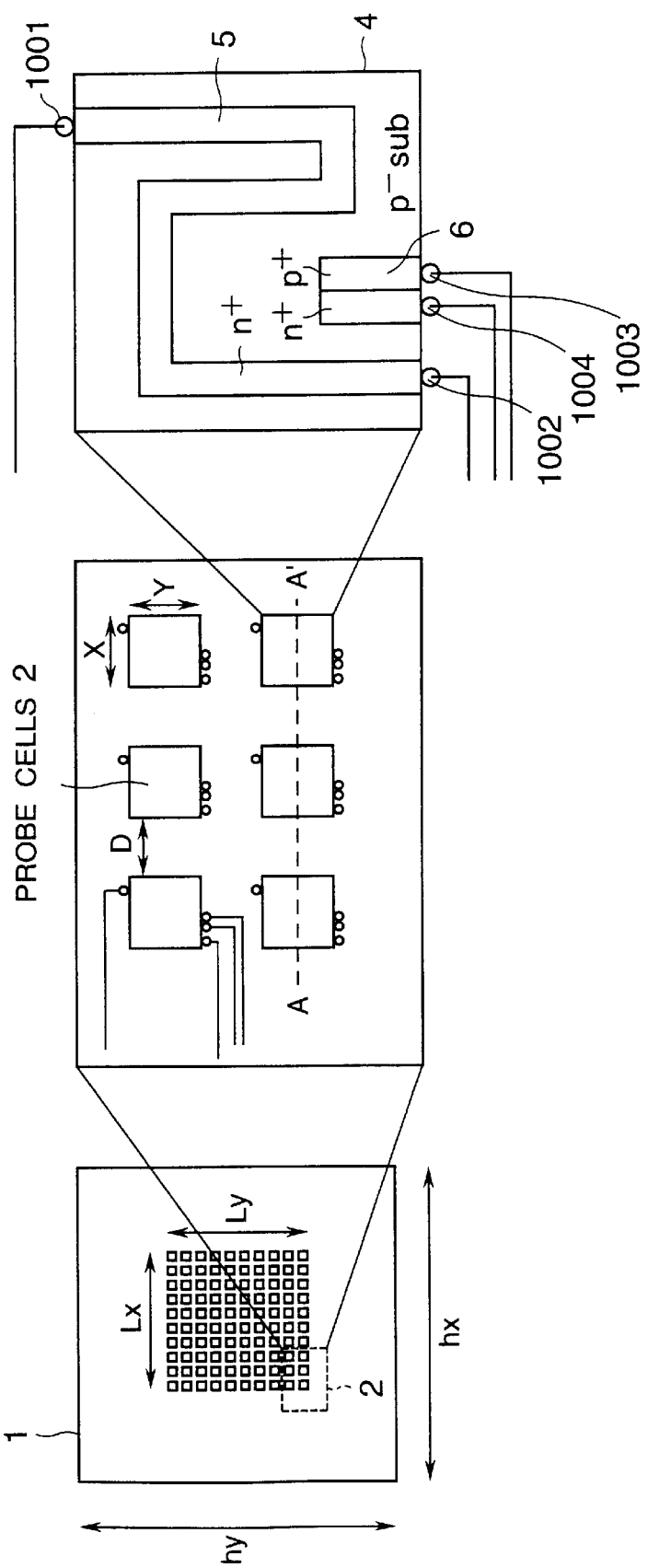

A CROSS SECTION VIEW AT A-A'

AN ENLARGED BACKSIDE PICTURE

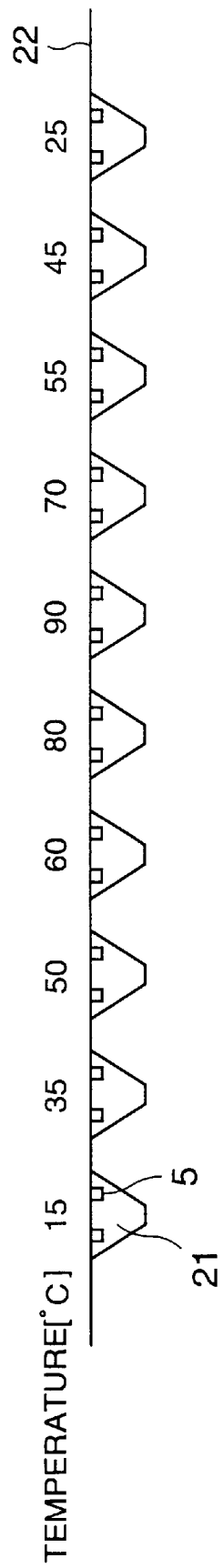

AN ENLARGED BACKSIDE PICTURE

A CROSS SECTION VIEW AT B-B'

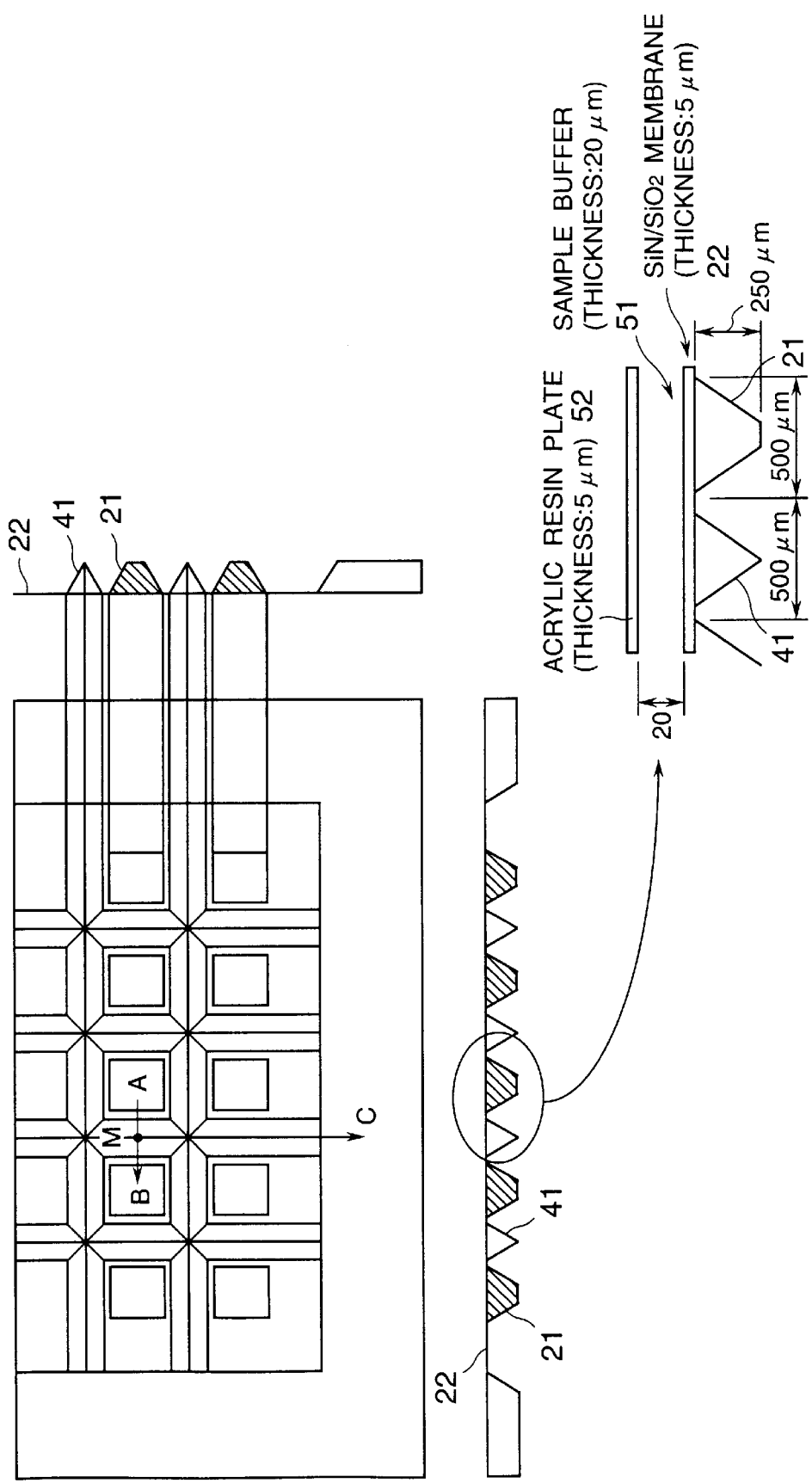

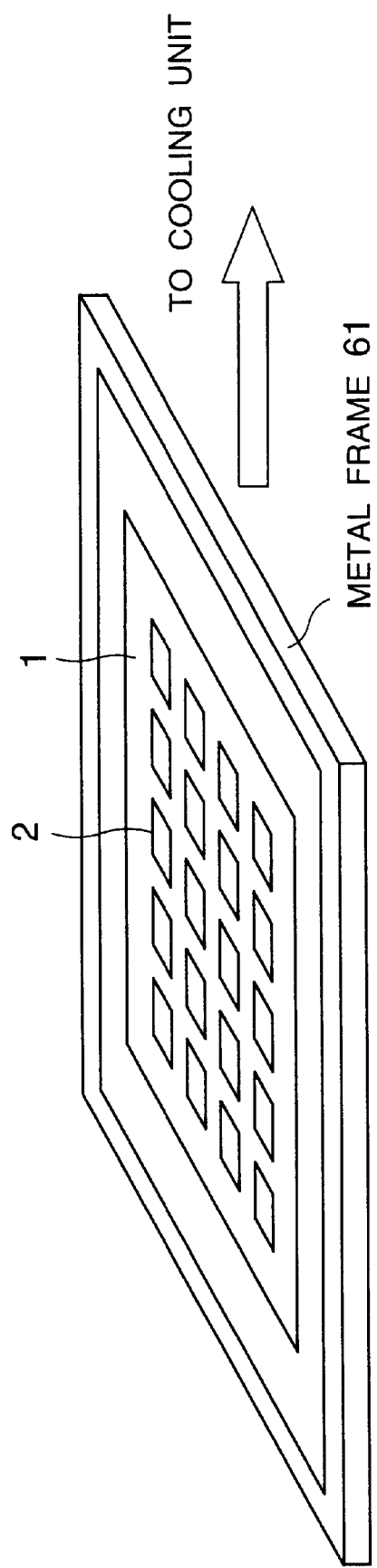

FIG.12A
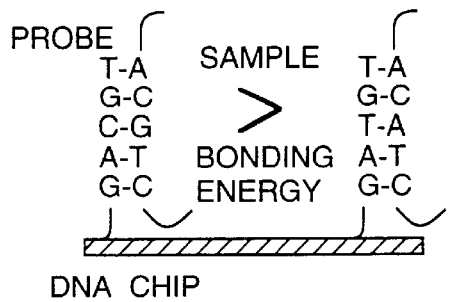
FIG.12B
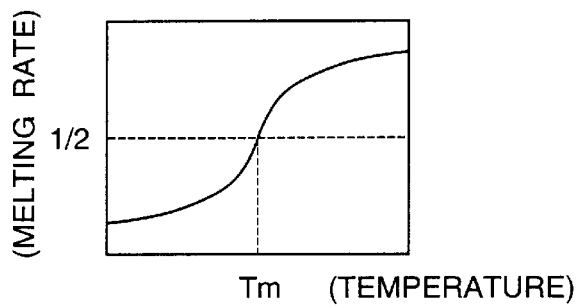
FIG.12C
8-MER PROBE EXAMPLE
|  | MIN. | MAX. | ΔTm |
|---|---|---|---|
| PROBE | ATATATAT | GCGCGCGC |  |
| Tm *1 | 15.2 | 56.2 | 41.0 |
*1 : APPROXIMATE VALUE(%GC METHOD)
FIG.13
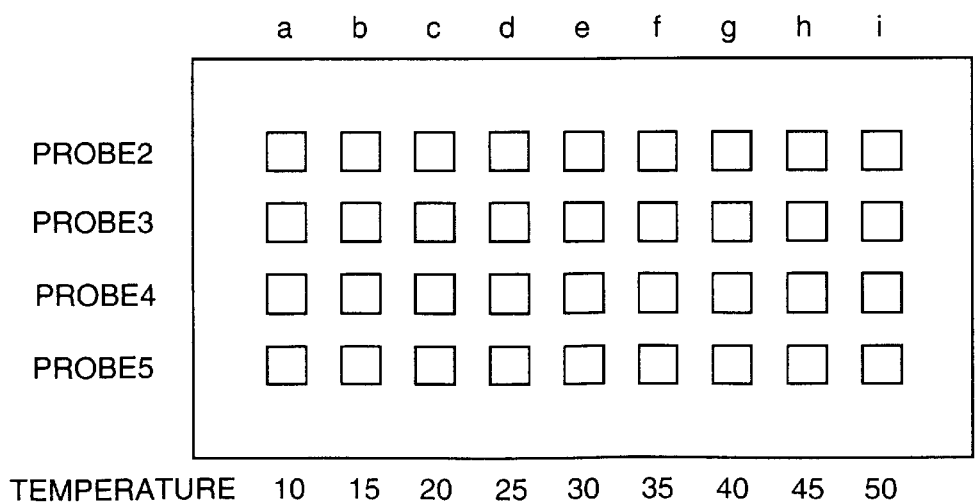

EXAMPLE II

EXAMPLE III

DNA CHIP TEMPERATURE-VOLTAGE CHARACTERISTIC

ADVANCED THERMAL GRADIENT DNA CHIP (ATGC), THE SUBSTRATE FOR ATGC, METHOD FOR MANUFACTURING FOR ATGC, METHOD AND APPARATUS FOR BIOCHEMICAL REACTION, AND STORAGE MEDIUM

BACKGROUND OF THE INVENTION

The present invention relates to an advanced thermal gradient DNA chip (ATGC), a substrate for ATGC, a method of manufacturing of ATGC, a method and an apparatus for biochemical reaction and a storage medium.

DESCRIPTION OF THE RELATED ART

As a method for determining a base sequence of a nucleic acid, the method for detecting hybridization between a single stranded polynucleotide of interest and a single stranded oligonucleotide probe previously designed, by using the polynucleotide detection chip with the single stranded oligonucleotide probes immobilized on its different areas depending on the type of sequences,are known. Examples of the polynucleotide detection chips include polynucleotide detection chips for diagnosis, where DNAs complementary to specific mutated sequences of interest are arranged (Science, Vol. 270, 467–470, 1995) and those for SBH (Sequencing By Hybridization) method, in which the oligonucleotide probes capable of hybridizing with all the possible base sequences existing in a sample are provided on the chips, for determining the base sequences of the subjects of measurement (J. DNA Sequencing and Mapping, Vol.1, 375–388, 1991).

The thermal stability of hybridization between oligonucleotide probes and the single stranded polynucleotide varies depending on the types of base sequences. The reason for this is as described in the following. The bonding between adenine (A) and thymine (T) or adenine (A) and uracil (U) is of double hydrogen bond per base pair, while the bonding between guanine (G) and cytosine (C) is of triple hydrogen bond per base pair (see FIG. 11), resulting in some differences in bonding strength between these two types of bondings. Since the G—C bond is greater in strength than the A—T bond (see FIG. 12A), the thermal stability of the former is higher. Therefore, comparing the thermal stability of hybridization of sequences with equal base length, the thermal stability of hybridization involved by only A—T or A—U bond is lowest, while that involved by only G—C bond is highest. In general, the thermal stability of hybridization is represented by the temperature (melting temperature, hereinafter referred to as Tm) at which both bonding and dissociation exist at rate of 50% respectively (FIG. 12B).

Taking an example of the oligoucleotide DNA probe of octamer, the Tm of the duplex DNA which consist of the A-T bondings, is 15.2° C. (a value calculated by the % GC method (Breslauer K. J., et. al., "Predicting DNA Duplex stability from the base sequence", Proc., Natl. Acad. Sci., USA83, 3746–3750), while the Tm of the duplex DNA which consist of the G—C bondings, is 56.2° C., giving a difference of 41.0° C. (FIG. 12C).

As indicated above, when the value of Tm of the hybridization for each probe varies largely, it is necessary to carry out hybridization assay at Tm of each probe, respectively. When a temperature is higher than Tm, a single stranded polynucleotide is hard to bond effectively with a probe. On the other hand, when a temperature is lower than Tm, the background noise resulting from the mismatch bonding increases, leading to the decline of measuring resolution. Thus, in a case where different kinds of probes are immobilized on the polynucleotide detection chip, when the probes are hybridized with the single stranded polynucleotide sample while keeping the temperature constant on the chip, this gives rise to problems such as differences in the amount of the formation of hybridization and differences in mismatching probability occurring due to the difference in thermal stability among individual probes.

Conventionally, in order to resolve the above-described problems, an attempt has been made such as adjusting the salt concentration in solvent or varying the density or the base length of the probes to be immobilized on the detection chip for each probe, while keeping the temperature equal for hybridization for all the probes on the detection chip. Such an attempt, however, is not sufficient for fully eliminating the effect of the difference in Tm.

As an example of the means for resolving this problem, there is Laid Open Japanese Patent No. H11-127900 disclosing a method wherein conductive heating track is provided around each analytical electrode or a method wherein each analytical electrode is heated by means of laser. However, the Laid Open Japanese Patent No. H11-127900 discloses a method characterized by only heating the analytical electrode and no means controlling, for example, the temperature of the analytical electrode to a constant level, are disclosed.

SUMMARY OF THE INVENTION

An object of the present invention is to provide a biochemical reaction detection chip and its substrate capable of controlling the temperature for biochemical reaction including hybridization of the oligonucleotide probe with polynucleotide.

Another object of the present invention is to provide a apparatus and a method for enabling the biochemical reactions in a plurality of reaction systems to progress simultaneously at temperatures controlled for individual reaction systems and an associated data storage medium.

Further another object of the present invention is to provide a substrate of a biochemical reaction detection chip comprising a plurality of islands of a heat conductive material formed on a membrane, the islands being placed apart from each other and each island being provided with a temperature controller.

It is preferable for the membrane to be formed from a material having a high insulating ability, heat insulating ability and physical strength. The electric conductivity of $10^8$ Ω·m or more is sufficient for the membrane material, preferably, $10^{10}$ Ω·m or more. The heat conductivity of 10 w/mk or less is sufficient for the membrane material, preferably, 1 w/mk or less.

It is easier to control the temperature of each island by forming the membrane from a material having a high (electrical) insulating ability and a high heat insulating ability. The membrane may be formed, for example, from at least one of a group of materials such as silicon nitride, silicon oxide, aluminum oxide, $Ta_2O_5$, or may be a composite membrane of these materials. Among these, the composite membrane of SiN and $SiO_2$ is preferable. Since SiN has resistance to alkali, probes can be immobilized on SiN membrane by means of silane coupling in alkali solution. Further, the SiN membrane is capable of protecting the electronic circuit for temperature control provided thereunder from the solution such as sample solution.

The film thickness of 1–500 μm is sufficient, preferably, 5–20 μm.

It is preferable to make an indent for the area for fixing the probe of the membrane. Such indent is convenient for holding the sample solution on a chip when letting the biochemical reaction take place by bringing sample solution into contact with the probe.

Further, a resist membrane may be formed on the surface opposite to the islands. The resist membrane may be of a photosensitive polyimide resin or the like.

A plurality of islands of a heat conductor are formed on the membrane. "A plurality of islands" means at least 2 islands, preferably 10–1000 islands, although the number of the islands is not defined. A plurality of islands may be arranged either in line or 2-dimensionally, that is, in a first direction (row) and a second direction (column).

The islands are formed from a heat conductor. Examples of heat conductors include crystals of Si, metals such as Ag, Au, Cu and silicones such as polysilicone and amorphous silicone. The heat conductor constituting the islands is preferable to be electrically insulatable from the temperature controller. Silicone is preferable as a heat conductor to form the islands, since it is a good heat conductor and can be electrically insulated from the temperature controller. The insulation between the heat conductor and the temperature controller can be secured by forming a pn junction in the silicone.

The islands are spaced from each other. The spaces among the islands serve as a substitute for heat insulating material, and so the temperature of each island can easily be controlled independently.

The size of 10–1000 $\mu m^2$ is sufficient for an island, preferably 50–500 $\mu m$. The interval of 50–1000 $\mu m$ between islands is sufficient, preferably 100–500 $\mu m$. The shape of islands are not defined specifically. For instance, when forming the islands of Si crystal from a flat sheet of Si crystal having 100 planes as a surface by removing unnecessary portion by etching with KOH, 111 planes are exposed during manufacturing process, making a regular pyramid-like form.

Each of a plurality of islands is provided with the temperature controller. More particularly, it is preferable to provide a heating circuit and a temperature detection circuit for each island. The heating circuits and the temperature detection circuits may be controlled to operate independently either for each island or for each group of islands.

Further, where a plurality of islands are arranged two-dimensionally, the heating circuits and the temperature detection circuits may be controlled to operate independently for each (first or second) line. The size of the biochemical reaction detection chip is sufficient to be 25 $mm^2$–100 $cm^2$, preferably 100 $mm^2$–14 $cm^2$.

With a biochemical reaction detection chip manufactured by immobilizing probes on a substrate of the biochemical reaction detection chip according to the present invention, the influence of the temperature of an adjacent probe cell (reaction system) can be reduced so that the biochemical reaction is allowed to progress at a proper temperature on each of the probe cells (reaction system).

The substrate for the biochemical reaction detection chip according to the present invention is preferable to be provided with heat sinks for allowing heat to escape outside installed among the islands. Each heat sink is preferable to have a structure (e.g., a mesh structure) that prevents it from directly contacting with islands. The heat sinks may be installed either only for one direction or both directions of first and second directions. Where the probes are divided into groups according the proximity of optimal temperatures of biochemical reactions and fixed on the membrane, heat sinks may be provided for each area of such groups, respectively.

It is preferable to form heat sinks from materials having good heat conductivity, such as Si, Au, Ag, Cu and the like.

Forming heat sinks among the islands enables heat to escape outside before being transmitted from any adjacent islands.

The distance between an island and a heat sink is sufficient to be 10–500 $\mu m$, preferably 10–250 $\mu m$.

Further, the present invention relates to a method for manufacturing the substrate for the biochemical reaction detection chip, more particularly to a method comprising the steps of:

(a) forming a membrane on one surface of a flat sheet of heat conductor, and (b) forming islands of heat conductor by removing unnecessary portion from the other side of the flat sheet of heat conductor.

In the method mentioned above, temperature controller may be provided on one surface of the flat sheet of heat conductor, and the membrane may be formed thereon.

As one embodiment of the manufacturing method for the substrate of the biochemical reaction detection chip, a mask having a desired pattern may be provided on the surface of the flat sheet of heat conductor opposite to the surface the membrane is formed so that the masked surface can be etched until the membrane formed on the other surface comes to be exposed to form islands of heat conductor on the membrane corresponding to the pattern of the masking. The mask, for example, may be of a silicon nitride membrane.

Further, the present invention provides a biochemical reaction detection chip with a probe immobilized on the substrate of the biochemical reaction detection chip described above.

The surface of silicon nitride membrane is preferable for having the probes immobilized thereon. In this case, the probe with amino group can be immobilized on the surface of silanized silicon nitride membrane by means of silane coupling.

"Probe" means substances which can specifically detect a particular substance, site, state and the like, and includes oligonucleotide DNA/RNA probes, protein probes such as antibodies, and the like. In the case of oligonucleotide DNA/RNA probe, the number of bases is sufficient to be 4–500 nt (nucleotide), preferably 8–200 nt (nucleotide). The oligonucleotide probe may be either of single strand or double strand, preferably of single strand from the point of the efficiency of the bonding between the probe and the subject.

Probes can be immobilized on the membrane on the substrate of the biochemical reaction detection chip by a known method. For instance, when the probe cells on the membrane are silanized, a probe with amino group can be immobilized on the membrane by silane coupling. The islands should be provided under the probe cells on membrane.

Further, after the probe is immobilized, the area of the membrane other than that of the probe cell is preferable to be coated with polylysine to make inactive the binding site which is not binding to the probe of the silane coated surface. Polylysine coating can prevent sample DNA, RNA and the like from binding non-specifically with the silane coated surface.

The kinds of probes are not limited, and one or more kinds of probes may be used. When a plurality kinds of probes are immobilized on a single chip, a plurality subjects of detection in one sample can be detected simultaneously. Alternatively, when many kinds of probes are immobilized on a single chip, one kind subject of detection in a plurality of samples can be detected simultaneously.

The detection chip according to the present invention can be used for detecting biochemical reactions, for example, for detecting DNA, cDNA, RNA and protein, and antigen-antibody reaction.

When the biochemical reaction detection chip according to the present invention is used, the biochemical reaction can be carried out at an optimal temperature on each probe cell (reaction system) by reducing the influence of the temperature of adjacent probe cell (reaction system).

Further, the present invention provides a biochemical reaction apparatus for enabling the biochemical reactions in a plurality of reaction systems to take place on a biochemical reaction detection chip, the apparatus comprising a heater for heating the whole biochemical reaction detection chip to a temperature higher than the optimal temperature for each biochemical reaction and a temperature controller for controlling the temperature of each reaction system to a temperature suitable for each biochemical reaction.

The temperature controller is preferable to control the temperature of each reaction system by minutes.

Further, the present invention provides a computer-readable storage medium storing a program for operating a biochemical reaction apparatus for enabling the biochemical reactions in a plurality of reaction systems to take place on a biochemical reaction detection chip, the apparatus comprising a heater for heating the whole biochemical reaction detection chip to a temperature higher than the optimal temperature for each biochemical reaction, and a temperature controller for controlling the temperature of each reaction system to a temperature suited for each biochemical reaction.

The present invention also provides the reaction methods given below.

(1) A method for carrying out biochemical reactions in a plurality of reaction systems simultaneously at temperatures controlled respectively for each reaction system, comprising the steps of:
  (a) heating all the reaction systems to a temperature higher than the optimal temperature for the biochemical reaction in each reaction system, and
  (b) lowering the temperature of each reaction system to an optimal temperature for each biochemical reaction in each reaction system and maintaining the temperature for a certain period of time.

(2) A method according to (1) above, wherein the heating process (a) is carried out in an incubator.

(3) A method according to (1) above, wherein the process for lowering the temperature (b) is carried out by stopping heating process (a) or using a cooler.

(4) A method according to (1) above, wherein the biochemical reaction is the hybridization between polynucleotide and oligonucleotide, and the optimal temperature for the biochemical reaction is the melting temperature of double strand formed with the oligonucleotide and its complementary strand.

(5) A method according to (4) above, wherein the polynucleotide is DNA in a sample, and the oligonucleotide is oligonucleotide probe of the biochemical reaction detection chip.

Further, the present invention also provides a storage medium storing a program for performing the biochemical reaction controlled by a computer.

(6) A computer-readable strage medium storing a program for executing a method for performing a plurality of biochemical reactions in a plurality of reaction systems simultaneously while controlling the temperature for each reaction system, the method comprising the steps of:
  (a) heating all the reaction systems to a temperature higher than the optimal temperature for the biochemical reaction in each reaction system, and
  (b) lowering the temperature of each reaction system to an optimal temperature for each biochemical reaction in each reaction system and maintaining the temperature for a certain period of time.

When the optimal temperature for a biochemical reaction is the melting temperature of double strand formed with oligonucleodide probe and its complementary strand, the temperature higher than the optimal temperature for the biochemical reaction is preferably a temperature at which the double stranded nucletiode dissociates completely, for example, a temperature between 90° C.–99° C. The temperature suitable for the biochemical reaction may be a temperature around the melting temperature, e.g., within the melting temperature ±2° C.

An embodiment of the present invention will be described in the following. A sample is injected into reaction systems on a biochemical reaction detection chip. Then, the chip is covered and placed in an incubator and heated to a maximum temperature, e.g., 90° C. Normally, the incubator is provided with a heater and a cooler so that the internal temperature can be adjusted to a predetermined temperature. The temperature of the incubator is then set to a minimum temperature, e.g., 15° C., to bring down the temperatures of all the reaction systems. When the temperature of each reaction system (e.g., a probe cell) is become lower than a set temperature (e.g., a melting temperature of double strand formed with each probe and its complementary strand), the heater is turned on to proceed the biochemical reaction while maintaining the set temperature for each reaction system for a period of time (e.g., 12 hours). After the reaction, the reaction system (e.g., the probe cell) is washed, and the biochemical reaction is detected to process the data obtained as a result of the detection.

For detection, a fluorescent marker is generally bound to a sample so that the amount of fluorescence of the marker bound to the probe can be measured with a co-focal-point microscope, and the amount of the bonded sample is calculated on the basis of the amount of the fluorescence.

Normally, biochemical reactions started at an optimal temperature for the biochemical reactions only by heating the reaction systems. However, this method frequently results in the probe binding with a substance other the subject that to be detected, causing the noise in detecting the subject. Therefore, raising the temperature of reaction systems to a level higher than the optimal temperature for the biochemical reactions and then lowering to,the optimal temperature can reduce the probability that the probe is bound with a substance other than the subject of detection, thereby reducing the noise in detecting the subject.

For the hybridization of the oligonucleotide probe and polynucleotide, the optimal temperature is the melting temperature of the double strand formed with the probe and its complementary strand. When the reaction is allowed to proceed at the melting temperature only by heating the reaction system, the oligonucleotide probe may bind with a nucleotide other than the nucleotide having the complementary strand to the probe (the subject of detection), resulting in so-called mismatching that causes the noise in detecting the subject. However, when the temperature of the reaction system is once raised to a level higher than the melting temperature, and then lowered to the melting temperature, the probability that the probe is bound with a nucleotide other than the nucleotide having the complementary strand to the probe is reduced, thereby contributing to the decrease of the noise in detecting the subject. In the method according to the present invention, the temperatures of all the reaction systems are first raised to the levels higher than the optimal temperatures for reactions and then lowered to the optimal temperatures, and maintained the temperatures for a certain period of time, for example, by supplying necessary amount of heat to the reaction system by heaters.

Consequently, comparing with the method in which the temperature of each reaction system is raised to its optimal temperature and the reaction is proceeded while maintaining the temperature, the present method not only reduces the total amount of the heat to be supplied to the reaction system but also controls the temperature for each reaction system more easily. The method according to the present invention is advantageous over the conventional method in performing a number of biochemical reactions in pararell-proceeding.

Alternatively, optimal temperature for one specific reaction can be determined when the method described above is applied to a plurality of reaction systems performing the same reaction at temperatures varying from system to system.

This specification includes part or all of the contents as disclosed in the specification and/or drawings of Japanese Patent Application No.356433/1999, which is a priority document of the present application.

BRIEF DESCRIPTION OF THE DRAWINGS

FIGS. 1A to 1C are schematic diagrams showing the substrate of a biochemical reaction detection chip for immobilizing oligonucleotide DNA(hereinafter referred to as DNA chip substrate). FIG. 1A is a plan view of DNA chip substrate 1 having 100 probe cells 2 in total comprising 10 rows in horizontal direction and 10 columns in vertical direction. FIG. 1B is a partial enlarged view of the framed area of 1A, and FIG. 1C is a partial enlarged view of one probe cell 2 shown in 1B.

FIG. 2A is a partial enlarged view of the back side of the DNA chip substrate. FIG. 2B is a vertical sectional view along dotted line A–A' of FIG. 1B.

FIG. 3 is a diagram showing an example of the temperature setting for DNA chip.

FIG. 4A is an enlarged backside view of DNA chip substrate and FIG. 4B is a vertical sectional view along dotted line A–A' of the DNA chip substrate 1 with the mesh structure formed thereon.

FIG. 5 is a diagram illustrating the effect of the mesh structure.

FIG. 6 is a diagram illustrating one embodiment of providing a cooler along the periphery of the mesh structure.

FIGS. 12A to 12C are diagrams illustrating the Tm value of hybridization varying according to the kind of probe. FIG. 12A shows that the bonding strength between the probe immobilized on the DNA chip substrate and the polynucleotide in sample solution varies according to the sequence of the probe. FIG. 12B is Tm curve of hybridization. Y-axis represents the degree of dissociation of the DNA double strand, and x-axis represents the temperature. FIG. 12C shows the Tm of the 8-base probes calculated by % GC method.

FIG. 13 is a plan view of a DNA chip.

DETAILED DESCRIPTION OF THE INVENTION

Figure 2B:
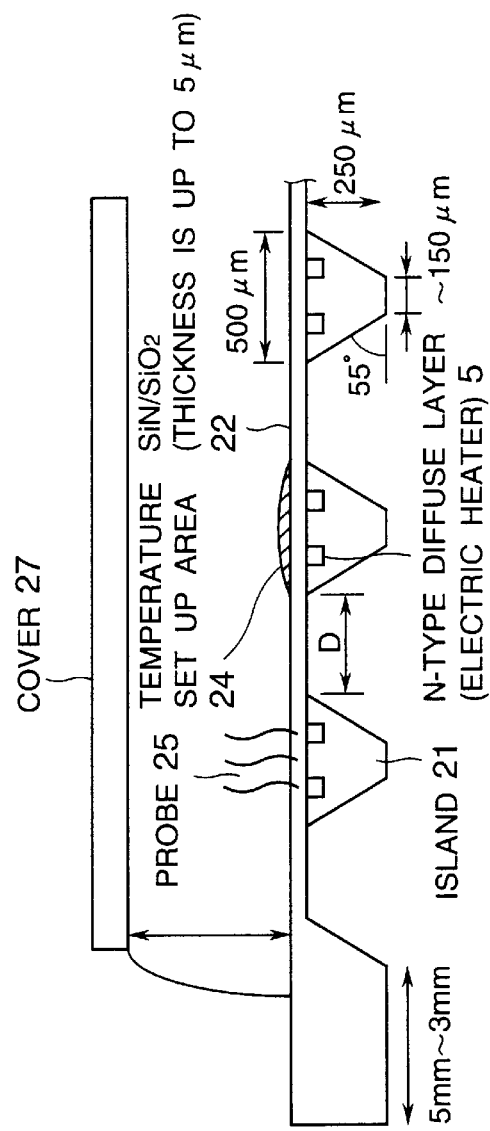
FIGS. 2A and 2B are diagrams illustrating the shapes of islands formed on the membrane.

The components of the present invention and corresponding reference numerals will be described in the following. 1, the substrate for DNA chip; 2, probe cell; 4, island; 5, heater circuit; 6, pn-junction temperature detection element; 1001, heater terminal (+); 1002, heater terminal (−); 1003, temperature detection terminal (+); 1004, temperature detection terminal (−); 21, Si island; 22, SiN/SiO$_2$ membrane; 24, temperature set up area; 25, probe; 26, sample solution; 27, cover; 41, mesh structure (heat sink); 51, sample buffer; 52, acrylic resin plate; 61, metal frame; 71, n-type substrate; 72, p-well; 73, p-well; 74, SiO$_2$ membrane; 75, n-type diffuse layer; 76, n-type diffuse layer; 77, n-type diffuse layer; 78, p-type diffuse layer; 79, p-type diffuse layer; 81, isolation between the first layers; 82, wiring in the first layer; 83, isolation between the second layers; 84, wiring in the second layer; 91, Si$_3$N$_4$ membrane; 101, DNA chip; 102, printed circuit board; 103, holder; 104, cable; 105, controller; 106, incubator; 107, fan; 108, cooling unit; 109, switch; 110, voltmeter; 111, output controller; Vpo, power source of heater; Vc, constant-voltage power source; 801, common wiring of sensor; 802, positive terminal of pn junction temperature sensor; 803, electrode; 804, electrode; 805, common electrode of sensor; 806, common electrode of heater; 901, side of island.

The embodiments of the present invention will be described referring to the drawings.

EXAMPLE 1

Structure of Substrate for DNA Chip

FIG. 1 is a diagram schematically illustrating a substrate for biochemical reaction detection chip for immobilizing oligonucleotide DNA (hereinafter referred to as substrate for DNA chip). The substrate for DNA chip immobilized probe is called a DNA chip.

FIG. 1A is a plan view a substrate for DNA chip carrying 100 probe cells in total, comprising 10 rows (in horizontal direction) and 10 columns (in vertical direction). The substrate for DNA chip is preferable to have vertical length (hy) and horizontal length (hx) of 10–100 mm respectively. The distance Lx from the left-end of the 1st probe cell to the right-end of the 10th probe cell in horizontal direction, and the distance Ly from the upper end of the first probe cell to the lower end of the 10th probe cell in vertical direction are preferable to be 5–100 mm respectively.

FIG. 1B is an enlarged view of the framed area of FIG. 1A. The width X and length Y of each probe cell on the substrate for DNA chip for immobilizing probes are preferable to be 10–1000 μm respectively. The intervals among the probe cells are preferable to be 50–1000 μm respectively.

An island is formed under each probe cell. FIG. 1C is a partially enlarged view of the probe cell 2 of FIG. 1B. Each probe cell is provided with a heater circuit 5 formed with n-type diffuse layer, and a temperature detection element 6 formed with pn junction between p-type diffuse layer and n-type diffuse layer. A heater terminal (+) 1001 and a heater terminal (−) 1002 are formed at both ends of the heater circuit 5. When a voltage is applied across both terminals so that the 1001 side is to be a positive electrode, current flows in the n-type diffuse layer 5 to produce Joule heat. The amount of Joule heat can be controlled by controlling either the level or duration of applied voltage. The temperature detection element 6 is provided with the temperature detection terminal (+) 1003 connected to the p-type diffuse layer and the temperature detection terminal (−) 1004 connected the n-type diffused layer. The current-voltage characteristics of pn junction of the temperature detection element 6 is largely dependent on the temperature of the pn junction. Therefore, the temperature of the pn junction can be determined by detecting the current-voltage characteristics between elements. Further, since the island 4 is made of a thermal conductor, the temperature of the pn junction and the temperature of the island 4 are almost equal to each other, and thus the temperature of the probe cell 2 on the island 4 can be detected by measuring the current-voltage characteristics between pn junction elements. The temperature dependency of the current-voltage characteristics at pn junctions, for example, in the case where the voltage is fixed in a forward bias with 1003 as being positive, the flow of the current varies exponentially with the temperature of the pn junction. Alternatively, when the current is fixed in a forward bias, the temperature and potential difference can be approximated on the basis of the linear function.

Figure 18:
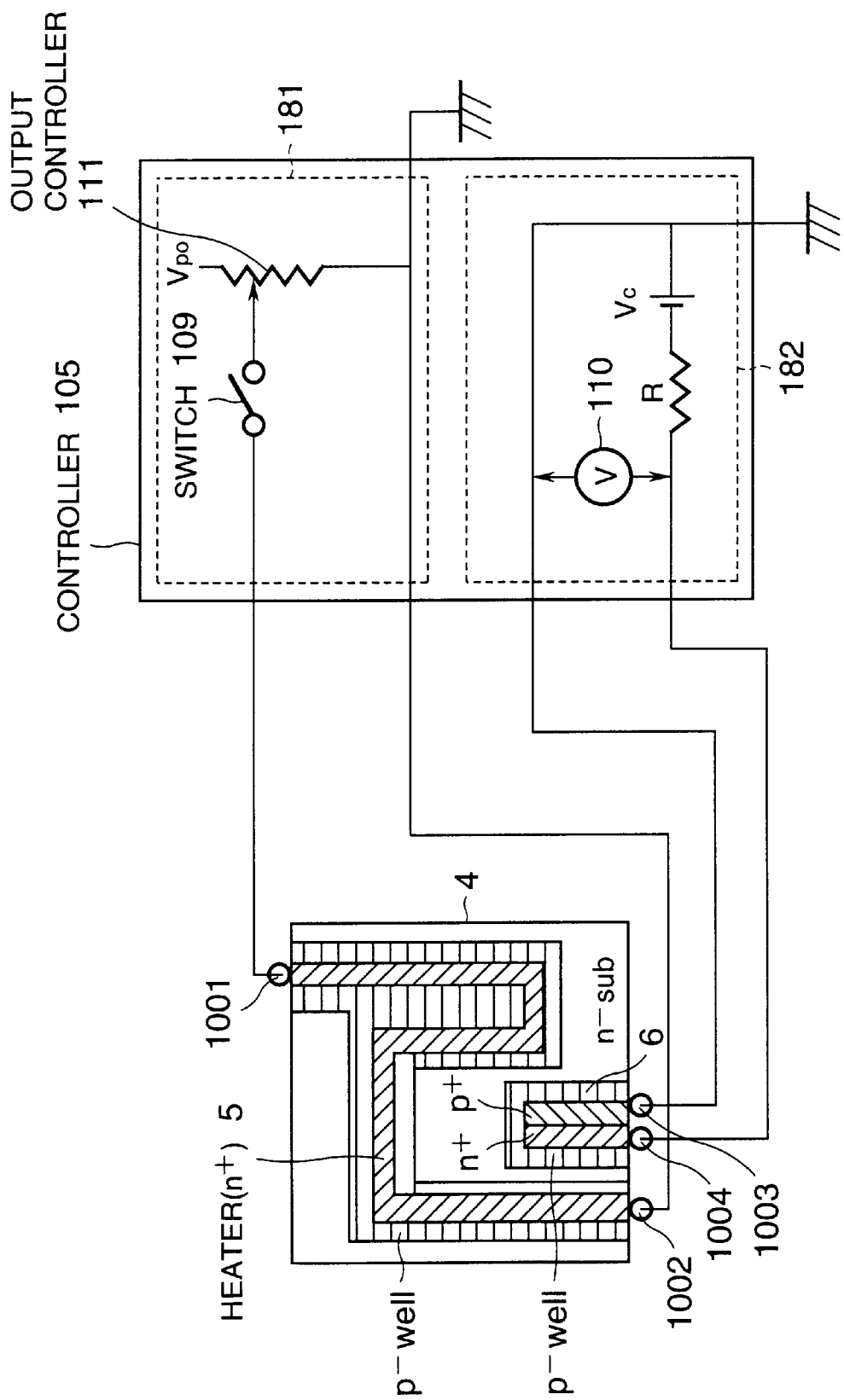
FIG. 18 is a diagram showing an example of the shapes of the heater circuit and temperature detection element in probe cell.

FIG. 18 shows another embodiment of the heater circuit and the temperature detection element of a probe cell. In this embodiment, an n-type substrate (n-sub) is used, and the heater circuit 5 and the temperature detection element 6 on a probe cell are separated by means of separate p-wells in order to make the heater circuit and the pn junction element electrically independent. This arrangement is designed for preventing the electrical interference between the n-type diffuse layer and the temperature detection element 6. As shown in FIG. 18, the probe cell is connected to controller 105 which comprises heater power source circuit 181 and temperature detection circuit 182. The controller 105 is an example of a circuit to detect the temperature of a probe cell and control heating by the heater. The heater power source circuit 181 comprises heater power source Vp, output controller 111 and switch 109, and is connected to terminals 1001 and 1002 of the probe cell. By controlling the heater power source Vp and the output controller 111, the voltage and the current across the terminals 1001 and 1002 of the probe cell, and therefore the Joule heat occurring in the heater circuit 5 of the probe cell, may be controlled. Temperature detection circuit 182 comprises power source Vc, resistance R and voltmeter 110. Terminal 1003 is set to zero potential, and terminal 1004 is connected to negative potential. In this case, forward bias is applied. When circuit resistance R is set up to have a sufficiently larger value than the resistance r between pn junctions, the current flowing through the temperature detection circuit 182 is substantially dependent on the power source Vc and the resistance R, and can be approximated at a constant-current condition of the formula: the current I=Vc/R.

The potential difference between temperature detection elements can be measured by voltmeter 110.

Figure 19:
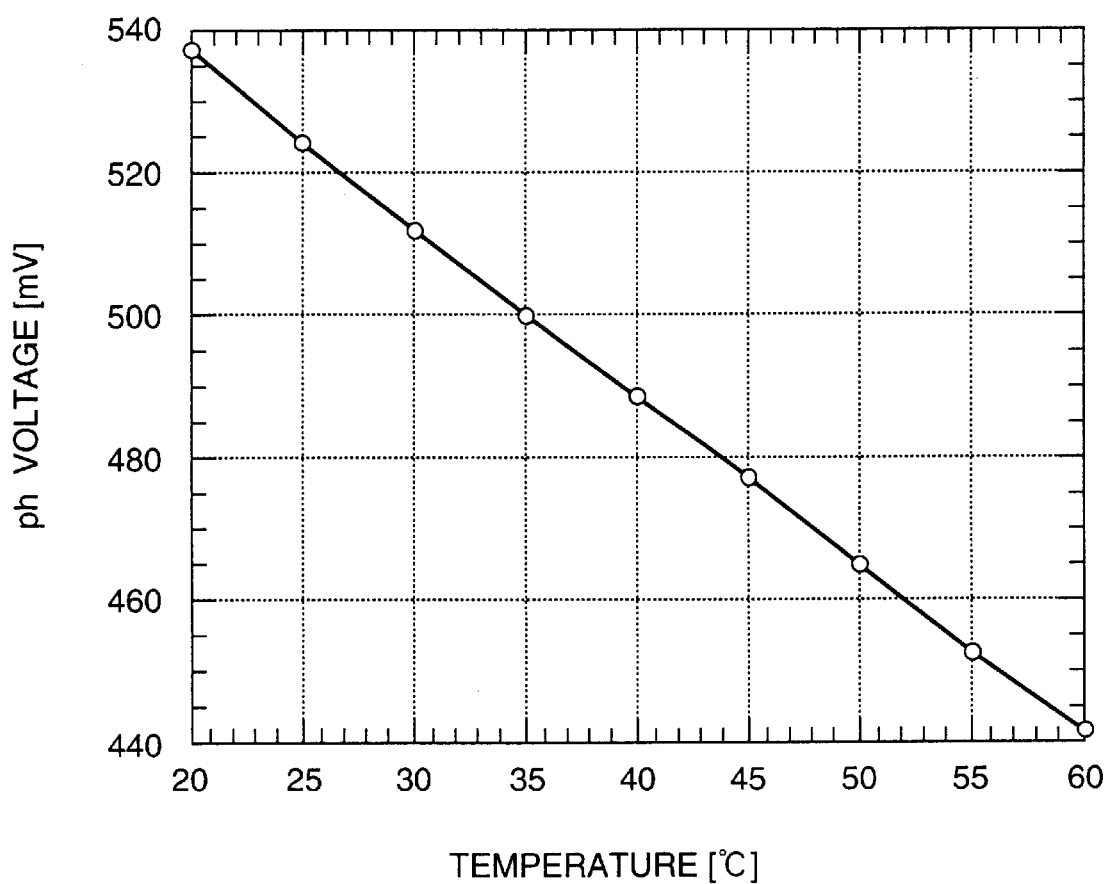
FIG. 19 is a graph showing the relationship between the temperature (t) of the probe cell and the temperature detection element (v) in the temperature detection circuit of FIG. 18.

The principle on which the temperature could be detected will be explained in the following. FIG. 19 is a graph showing the relationship between the temperature of the probe cell (t) and the potential difference between the temperature detection elements 6 (v) shown in FIG. 18. The temperature of pn junction is varied from 20° C. through 60° C. under the conditions of R=800 (KΩ), Vc=8 (V) and I=10 (μA).

| Temperature of Temperature Detection Element (° C.) | Potential Difference between Temperature Detection Elements (mV) |
| --- | --- |
| 20.0 | 537 |
| 25.0 | 524 |
| 30.0 | 512 |
| 35.0 | 500 |
| 40.0 | 489 |
| 45.0 | 477 |
| 50.0 | 465 |
| 55.0 | 453 |
| 60.0 | 442 |

According to the above result of experiment, the relationship between the potential difference Vx and the temperature Tx can be approximated in terms of a linear function having a gradient of about −2.37 (mV/° C.), and the following formula can be obtained.

$$Tx = 20 + (537 - Vx)/2.37$$

By using the formula above, the temperature can be determined by the measurement of potential difference with the temperature detection element.

Figure 20:
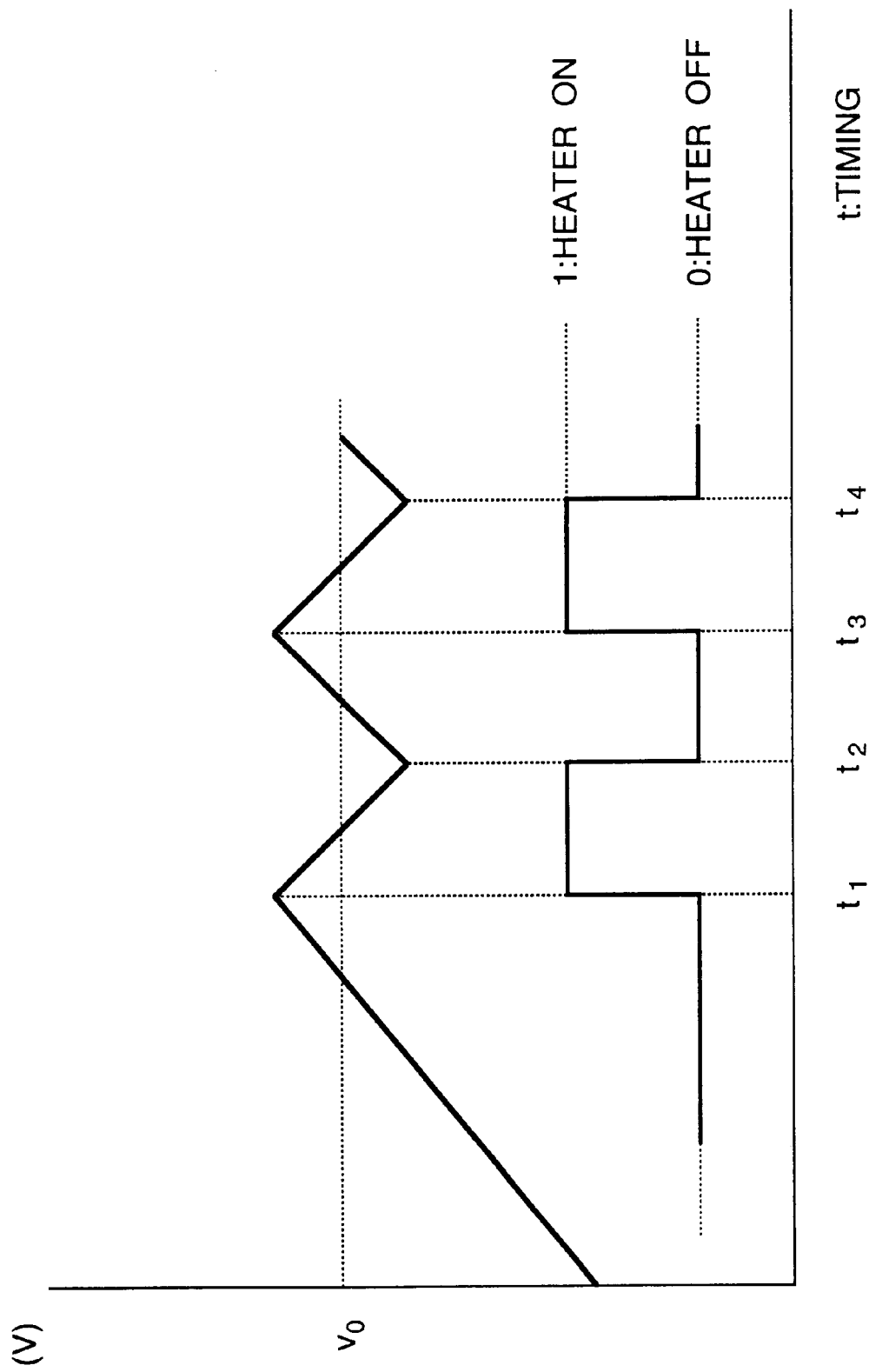
FIG. 20 is a diagram showing the voltage to be applied to the operating electrode and the timing of heating by the heater.

The voltage to be applied to operating electrode and the timing of heating by the heater will be described referring to FIG. 20. When the temperature to be set for the island 4, that is, the desired temperature of pn junction is given as $T_0$, the potential difference $v_0$ under this condition will be the target potential difference of the pn junction. When a sufficiently high temperature is set as an initial condition, the heater for heating the island being off, then the temperature falls according to the characteristics shown in FIG. 19, and the potential difference of pn junctions will increase. At the timing t1 when the potential difference of the pn junctions has exceeded v₀, the heater is turned on to heat the island. As a result, the temperature of the island increases, and the potential difference of the pn junctions decreases. At timing t2 when the potential difference has become lower than the target potential difference $v_0$, the heater for heating the island is turned off to stop the heating of the island. As the temperature of the island falls, the potential difference of the pn junctions resume increasing. By repeating such controlling, the potential difference $v_0$ of the pn junction, that is, the target temperature $T_0$ can be maintained.

The structure described above may be used to measure the temperature of the probe cell 2, and control the temperature by controlling the amount of Joule heat.

FIG. 2 is a diagram illustrating shapes of the island formed on a membrane.

Figure 2A:
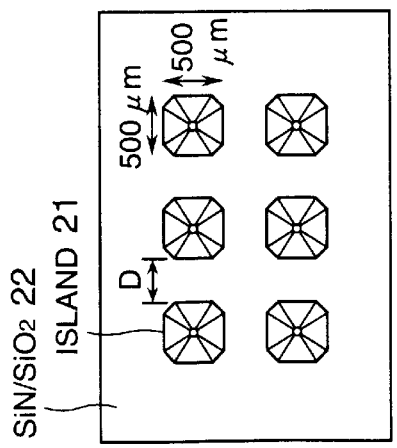

FIG. 2A is an enlarged backside picture of the substrate for DNA chip. Si island 21 is formed on a SiN/SiO₂ membrane 22. Both the width and the length of of the Si island 21 are about 500 μm. The distance between each Si island is substantially equal to the distance between each probe cell.

FIG. 2B is a cross section view at A–A' in FIG. 1B. The height of the Si island 21 is 250 μm. The length of the base of the Si island 21 is about 150 μm. The angle of inclination of the inclined side of the island 21 is about 55°. The Si island 21 incorporates the heater circuit 5 of n-type diffuse layer. The distance between each Si island is 500–700 μm. The thickness of the SiN/SiO₂ membrane 22 where the island is formed (i.e., the area of probe cell) is about 5 μm. In the peripheral area (the area of 3–5 mm from the edge of the membrane), the thickness of the Si layer is 250 μm.

The area on the SiN/SiO₂ membrane 22 matching with underlying Si island 21 is temperature set up area 24. Probe 25 is immobilized in this area.

By silanizing the probe cell on the membrane (silicon nitride membrane surface) and supplying amino group to the probe, the probe can be immobilized on the membrane by means of silane coupling.

Sample solution 26 is preferably added in the amount sufficient for making the solution layer with a thickness of 10–1000 μm. After addition of sample solution 26, a glass cover 27 is placed thereon.

FIG. 3 shows an example of the temperature setting for DNA chip. The temperature of each island is set to 15–90° C. As in FIG. 3 showing the arrangement of the probe cells for temperature setting, the probes may be arranged according to their Tm value. For example, probes may be arranged so that those with higher Tm values are placed in central area. while those with lower Tm values are placed toward peripheral area. Alternatively, the probes may be arranged from one side of the chip to the other side, by placing probes from those with highest Tm to those with lowest Tm. By arranging the probes in this manner, a good balance between the dispersion and supply of the heat can be maintained for easier temperature control.

FIG. 4 is a diagram illustrating the shapes of the islands and the mesh structure formed on the membrane.

Figure 4A:
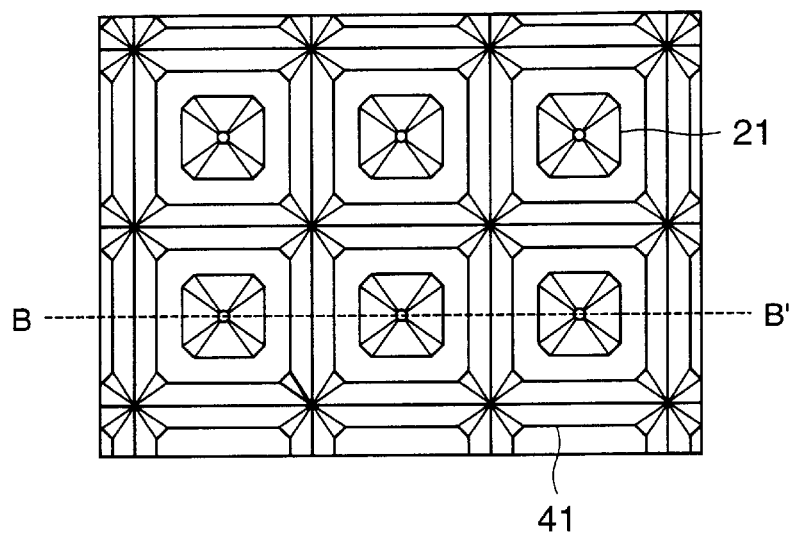
FIGS. 4A and 4B are diagrams illustrating the shapes of the islands formed on DNA chip and mesh structure.

FIG. 4A is an enlarged backside picture of a DNA chip substrate. Besides the Si island 21, the mesh structure 41 is formed on the SiN/Si₂ membrane 22 between the islands.

Figure 4B:
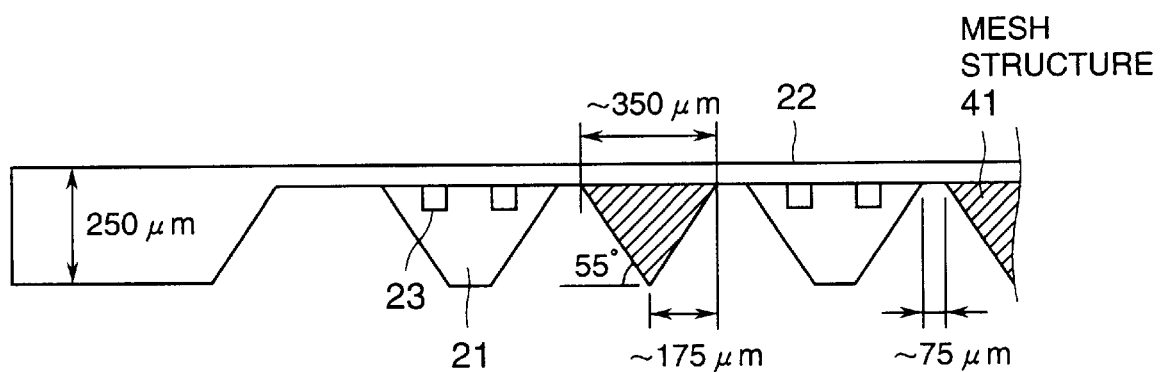

FIG. 4B is a cross section view at B–B' in FIG. 4A. The peak of Si constituting the mesh structure is about 250 μm high and about 350 μm wide. In this embodiment, the angle of inclination of the inclined side of the peak of Si is about 55°. The distance between the peak of Si constituting the mesh structure and the Si island 21 is about 75 μm.

With thermal conductor layer (mesh structure) 41 formed among the islands 21, it becomes possible to make the heat of any islands escape before being transmitted to an adjacent island. That is, the mesh structure serves as a heat drain.

FIG. 5 is a diagram illustrating the effect of the mesh structure. The conditions for producing this effect is as described in the following. The width and the length of the Si island 21 are 500 μm, respectively. The height of the Si island 21 is 250 μm. Both sides of the base of the Si island 21 is 150 μm. On the other hand, the height and the width of the Si constituting the mesh structure are about 250 μm and 350 μm, respectively. The distance between the peak of Si constituting the mesh structure and the Si island 21 is about 75 μm. The thickness of SiN/SiO₂ membrane 22 is 5 μm. The thickness of the water layer 51 (e.g. sample buffer) is 20 μm. The thickness of acrylic resin plate is 5 μm.

The heat conductivity from point A (the center of the base of Si island) to point B (the center of the base of an neighboring Si island) and the heat conductivity from the point A to point C (the point 2 mm apart from the middle point M between the point A and the point B) are compared. The heat conductivity from the point A to the point M is the same in both cases, and thus omitted from the comparison. Comparing the heat UMB transmitted from the point M to the point B per unit time with the heat UMC transmitted from the point M to the point C per unit time, where the heat transfer coefficient of the membrane is 10, and that of the Si layer is 150, the relationship of the UBC and UMC can be expressed as below.

$$UMB:UMC=10\times(\text{Sectional area of membrane})/150:150\times(\text{Cross sectional area of mesh structure})/2000=10\times(5\times500)/150:150\times(175\times250)/2000=1:20$$

Consequently, it can be found that the heat conduction from the point M to the point C is about 20 times as much as the heat conduction from the point M to the point B.

FIG. 6 is a diagram illustrating an embodiment provided with the cooling function on the periphery of the mesh. For example, a DNA chip substrate 1 is fit in metal frame 61 which is connected to a cooling unit. By providing the cooling function on the periphery of the mesh structure, the heat drain effect can be increased.

EXAMPLE 2

Chip Manufacturing Process

Figure 7:
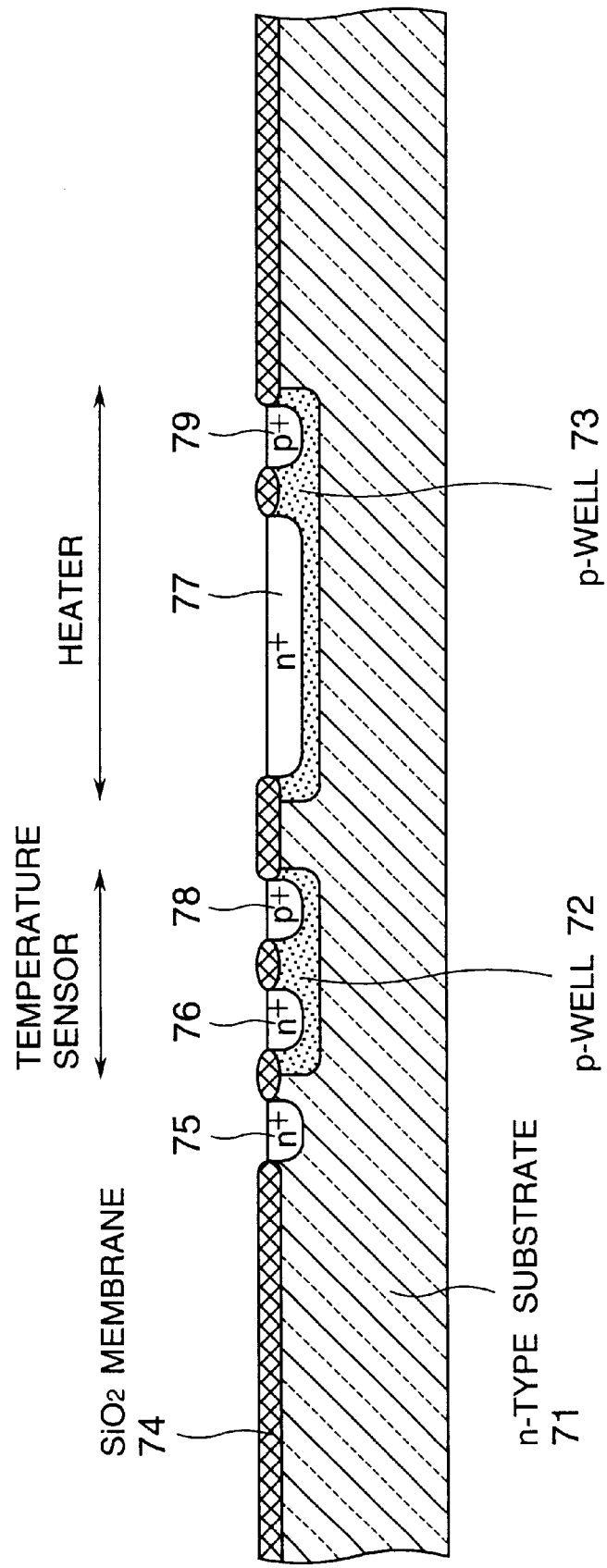
FIG. 7 is a diagram illustrating the first process for manufacturing DNA chip substrate.
Figure 8:
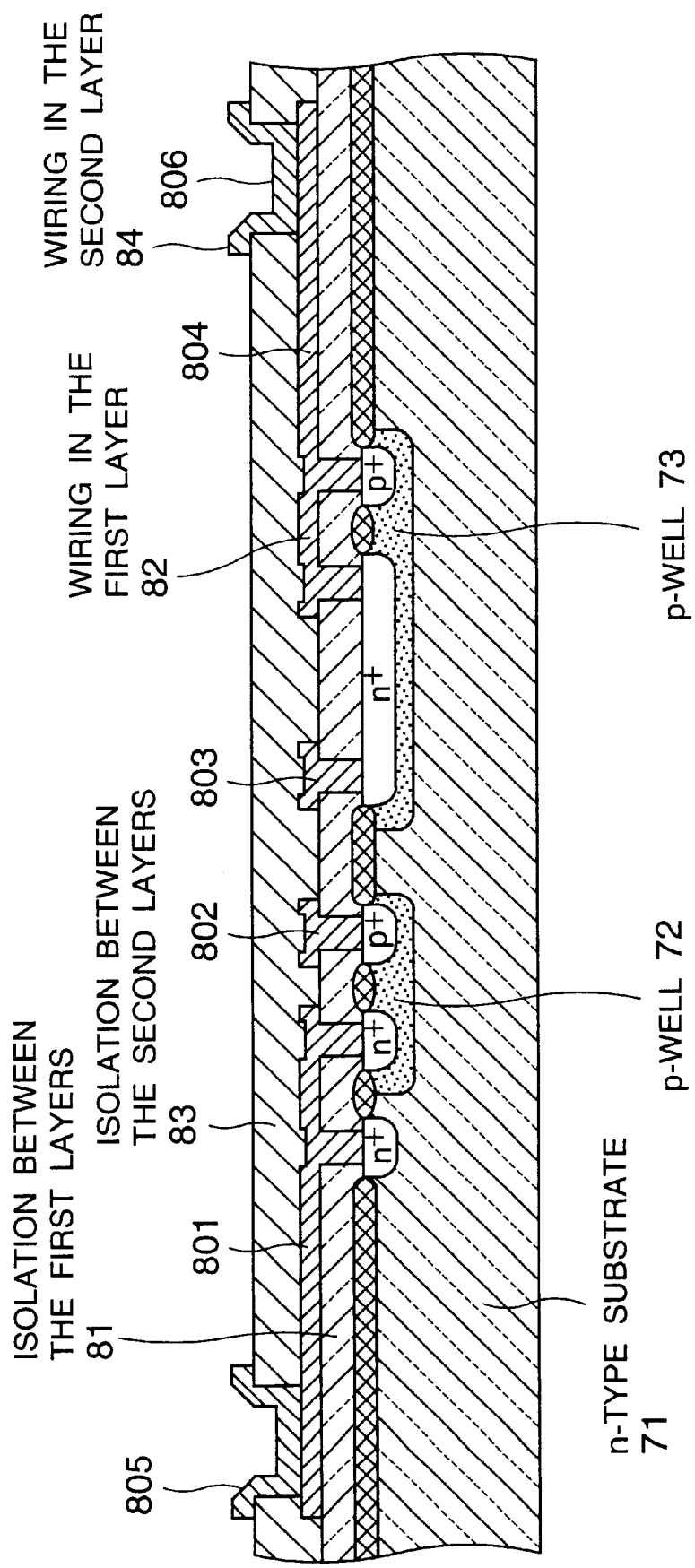
FIG. 8 is a diagram illustrating the second process for manufacturing DNA chip substrate.
Figure 9:
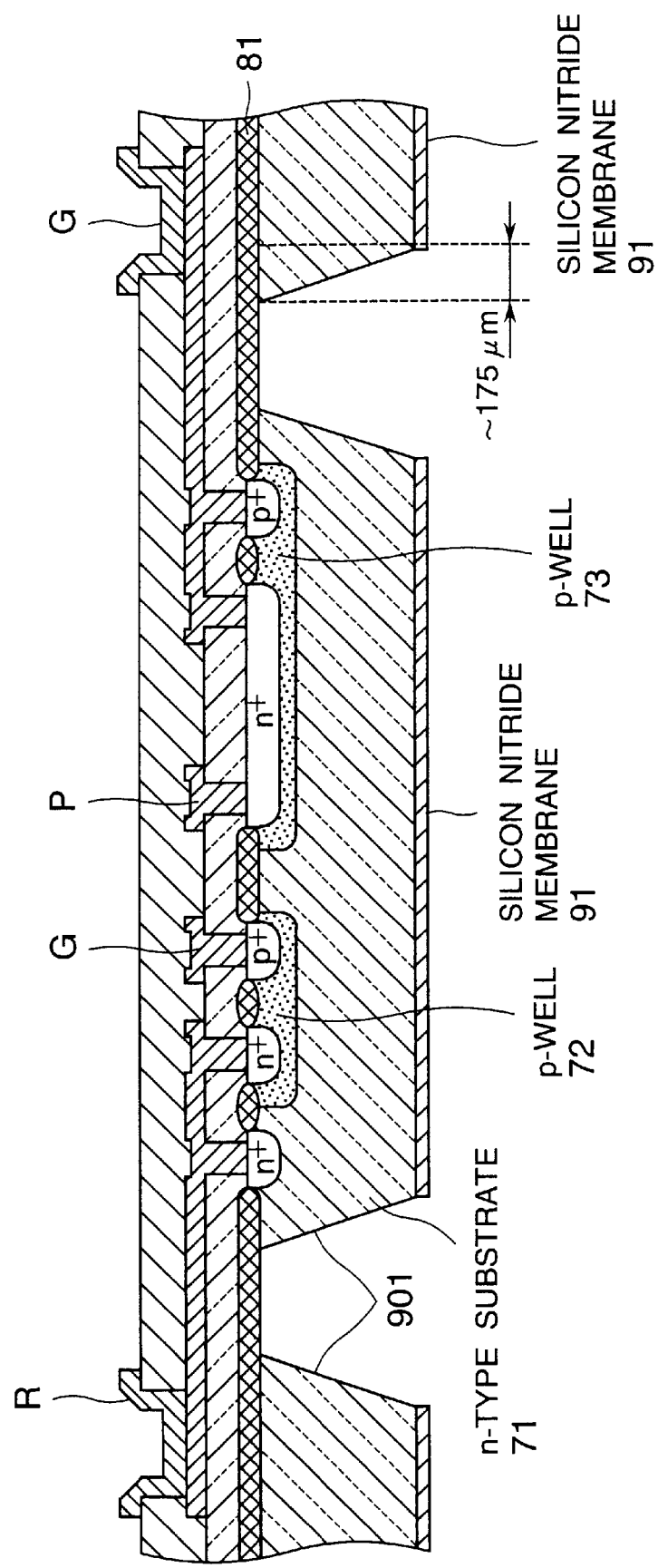
FIG. 9 is a diagram illustrating the third process for manufacturing DNA chip substrate.

Referring to FIG. 7 through FIG. 9, the manufacturing process of the DNA chip substrate, on which the islands are formed in the mesh structure on a composite membrane of SiO₂ and SiN, will be described.

FIG. 7 is a diagram illustrating the first manufacturing process of the DNA chip substrate. In this embodiment, an n-type Si substrate (N-sub) 71, having plane (100) as a surface area and thickness of 500 μm, is used as a substrate. After forming p-well pattern with the SiO₂ membrane 74 on the surface of the substrate, p-wells (1018 pieces/cm³) 72 and 73, having a depth of 3 μm, respectively, are formed by B doping and diffusion, in order to electrically insulate the temperature detection element 6 to be formed later by n+ diffusion and heater circuit 5. An SiO₂ membrane 74 is formed as a mask for separating elements and for diffusion. A dope such as boric acid is used for the p-well diffusion. Then, after forming a circuit pattern with SiO₂ membrane, a high-concentration of n-type diffuse layers 75, 76 and 77 (n+, 1020 pieces/cm³) and a high-concentration of p-type diffuse layers 78 and 79 (p+, 1020 pieces/cm³), with the depth of 100 nm respectively, are formed by the diffusion of phosphor (a high-concentration of n-type impurity). The n+

(n-type diffuse layer) 76 constitutes the temperature detection element 6. The n+ (n-type diffuse layer) 77 constitutes the heater circuit 5. The n+ (n-type diffuse layer) 75 is a reference electrode terminal 75 of the n-type substrate. The potential of the substrate 71 can be set by the reference electrode terminal 75, and the potentials of the p-well 72 and p-well 73 can be set by 78 and 79 respectively. The p+ (p-type diffuse layers) 78 and 79 are formed, by the diffusion of boron (a high-concentration of p-type impurity), as the terminals for providing the reference potential of the p-well.

FIG. 8 is a diagram illustrating the second manufacturing process of the DNA chip substrate.

Subsequent to the first process, the isolation membrane 81 between the first layers (e.g., $SiO_2$ membrane) is formed for protecting and insulating the surface circuit. The membrane 81 is formed by laminating BPSG membrane of 500 nm thick, on CVD oxidized membrane ($SiO_2$) of 400 nm thick, which has been formed previously. Then, after providing holes for each terminal in the isolation between the first layers 81, wiring in the first layer 82 (801, 802, 803, 804) are formed thereron as described in the following. The 75 and 76 are electrically connected to each other to form a common wiring 801 for the sensor. The 78 is connected to positive electrode 802 of pn junction temperature sensor. The temperature of the substrate can be measured by detecting the amount of current flowing between 802 and 801 via the p-well. Heater circuit 77 leads to two electrodes 803 and 804. The 804 is electrically connected to 79. The 804 is the common wiring for the heater circuit. When a power source is connected to between 803 and 804 with 803 as a positive electrode, the current for heating flows through 77 to generate Joule heat.

Next, a isolation between the second layers (e.g., SiN membrane) 83 is formed as a wiring protective membrane. The 83 is a laminated membrane comprising the $SiO_2$ membrane, 600 nm thick, of plasma DVD and the SiN membrane, 1,200 nm thick, of the plasma CVD. Then, after providing islation between the second layers 83 with connection holes for the wiring in the first layer, the wiring in the second layer (e.g., Au) 84 is formed. The 84 comprises for the common electrode 805 for the sensor connected to 801, the positive electrode of temperature sensor connected to 802 (not shown), positive electrode of the heater connected to 803 (not shown) and the common electrode 806 of the heater connected to 804. Of these components, 805 and 806 can be made common between a plurality of islands.

Lastly, an example of the island formed on the back will be explained. FIG. 9 is a diagram illustrating the third manufacturing process of DNA chip substrate. First, the back of an n-type substrate 71 is mechanically polished off to make the thickness of the substrate from 500 $\mu$m to 250 $\mu$m. This process is employed because 250 $\mu$m or less is sufficient for the thickness of island and reducing thickness results in the reduction of the time required for etching process. After smoothing the polished surface by chemical etching, silicon nitride membrane ($Si_3N_4$ membrane) 91 of plasma CVD is laminated to the thickness of 120 nm as an etching mask.

The pattern on the back (island pattern) corresponding to the previously formed devices on the opposite surface such as heater circuit, temperature sensor circuit and the like are matched with each other by using an aligner for both sides, and the silicon nitride membrane 91 is partially etched by dry etching method.

Next, with the remaining $Si_3N_4$ membrane 91 as the mask, the n-type substrate 71 is etched until $SiO_2$ membrane 81 is exposed, that is, until the silicon oxide membrane 74 on the surface side is reached by partially dissolving it with aqueous potassium hydroxide solution. Since the silicon nitride membrane 91 has an extremely high resistance to the aqueous potassium hydroxide solution, the amount which would be removed from the silicon nitride membrane during such etching of the Si substrate 71 having the thickness of 250 $\mu$m, is only 10 nm or less in thickness. Further, the etching rate for the plane (111) of the Si substrate 71 is as low as about 1/100 compared with that for plane (100). Consequently, the chip is etched along the plane (111) from the protective surface of the silicon nitride membrane 91, to be formed with the plane (111) exposed as the side surface 901 of the island. The plane (111) is inclined at angle of about 55° to the plane (100). Consequently, in the case of the etching of an Si substrate of 250 $\mu$m thick, a slope having the width of about 175 $\mu$m can be obtained.

EXAMPLE 3

Probe Immobilizing Process

The process for immobilizing oligonucleotide probes on a manufactured chip will be described in the following. First, OH group is introduced to the silicon nitride membrane on the surface of a chip. For this purpose, in general, the hydrolytic method by using the mixture of $H_2SO_4$ and $H_2O_2$, the mixture of NaOH and $H_2O_2$ and the like is employed. Further, the method in which the chip is simply left immersed in water for a certain period time is also applicable.

Next, a silane coupling agent such as the epoxy resin and the like is injected onto the surface of a chip to silanize the silicon nitride membrane. In this process, the previously introduced OH group combines with the silane coupling agent. In this embodiment, 3-glycidoxypropiltrimethoxy silane is used as a silane coupling agent. The reaction is carried out at room temperature for 30 minutes and followed by baking at 120° C. for 1 hour are given.

Next, oligonucleotide probes with amino group introduced at the end thereof are spotted on predetermined probe cell surfaces. By proceeding the reaction under a high-humidity condition at 50° C. for 10 minute for preventing drying of the substances, the probes can be immobilized on the surface of the chip by silane coupling. Next, an excessive amount of polylysine is injected onto the chip, and reacted under a high-humidity condition at 50° C. for 10 minutes to bind to the functional groups which are not binding to the probes. This process is effective for reducing the background resulting from the non-specific absorption during the process of hybridization with samples.

Lastly, the surface of the DNA chip is washed with Tris-EDTA, and the chip is dried for preservation.

EXAMPLE 4

Temperature Control

The apparatus for controlling the DNA chip will be described in the following.

Figure 10:
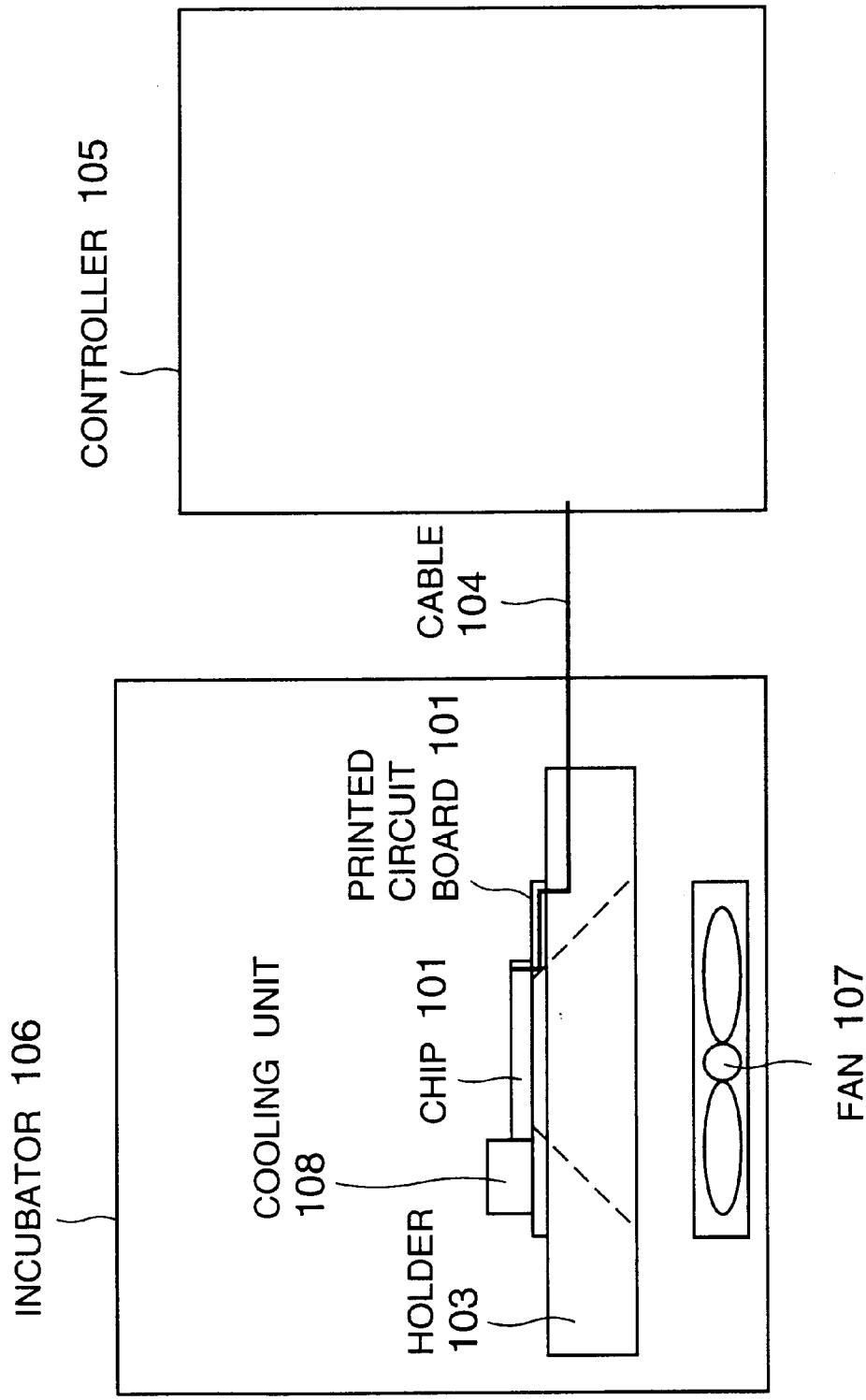
FIG. 10 is a diagram showing the structure of an example of the biochemical reaction detection apparatus.
Figure 11:
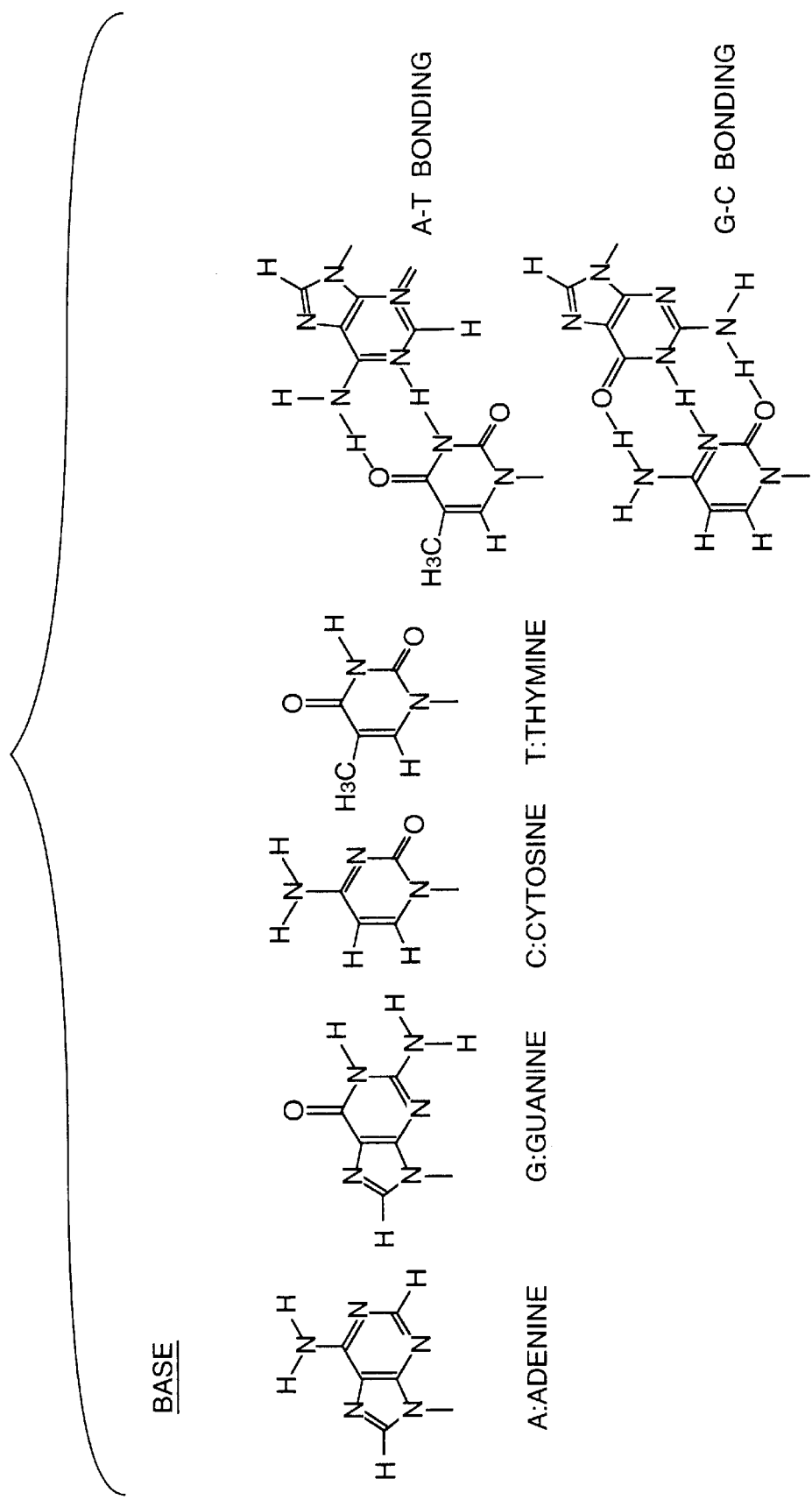
FIG. 11 is a diagram illustrating the bonding form between adenine (A) and thymine (T) and the bonding form between guanine (G) and cytosine (C). Dotted lines between O in molecular structure and H in molecular structure represent hydrogen bondings.

FIG. 10 is a diagram illustrating an example of the biochemical reaction detection apparatus. DNA chip 101 comprises probe cells, each provided with a heater terminal (+) 1001, a heater terminal (−) 1002, a temperature detection terminal (+) 1003 and a temperature detection terminal (−) 1004, and wiring for these terminals and controller 105 is similar to that shown in FIG. 18. The controller 105 comprises a temperature detection circuit 182, including a voltmeter 110, a power source Vc and a resistance R, and a heater power source circuit 181, including a heater power source Vpo, an output controller 111 and a switch 109, both of which are equivalent in number to the number of probe cells to be temperature-controlled independently from one another. FIG. 18 shows only one set of such components. Wirings to these terminals are connected to a holder 103 through a printed circuit board 102, and the holder 103 is further connected to a controller 105 through a cable 104. The wiring for the terminal connected to the grounding terminal on the side of the controller 105 can be used as a common wiring for a plurality of probe cells, for simplicity.

The temperatures of the individual probe cells can be controlled independently according to the method described above reffering to FIG. 18. The temperature of each probe cell can be determined by measuring the potential difference of the incorporated temperature detection element. The level of voltage to be applied across the heater is controlled by ON/OFF operation of switch 109 according to the measured value of the temperature. When the temperature detected from the temperature detection circuit is lower than the predetermined value, the switch 109 and the output controller 111 control the output from the power source of the heater $V_{po}$ to let the current flow in the heater. Controlling is performed to each probe cell independently.

The DNA chip 101, the printed circuit board 102 and the holder 103 are operated in a incubator 106, and a fan 107 is used when necessary for cooling the DNA chip 101 by sending the wind from below. The cooling unit 108 may be used for cooling the periphery of the DNA chip. In this embodiment, as will be described later, the temperature of the incubator is adjusted to a minimum value of various set temperatures required by the chip, and the cooling unit 108 and/or the fan 107 are used depending on the degree of the temperature raising of the chip or the temperature distribution among the probe cells arranged close to each other.

Further, the temperature of the DNA chip may be controlled with a computer. In this case, the computer serves as a temperature controller by incorporating a temperature control program which is stored in a computer-readable strage medium. The storage medium may be any type of storage medium such as RAM, ROM, magnetic disk, CD-ROM, magnetic tape, IC card.

EXAMPLE 5

Measurement

In this example, a measurement of a DNA fragment of 17-base length with 4 kinds of probes of 8-base length will be explained.

SEQ ID NO: 1 is a DNA fragment of 17-base length (hereinafter referred to as sample DNA).

TGACCGGCAGCAAAATG (SEQ ID NO: 1)

This sample DNA is hybridized with 4 kinds of 8-base-length probes given below.

CCGTCGTT (SEQ ID NO: 2)
CCCGTCGT (SEQ ID NO: 3)
GGCCGTCG (SEQ ID NO: 4)
TGGCCGTC (SEQ ID NO: 5)

The probe shown in SEQ ID NO: 2 (hereinafter referred to as probe 2) is a complementary sequence to the 6th through 13th bases of the sample DNA. Similarly, SEQ ID NO: 3 (probe 3), SEQ ID NO: 4 (probe 4), and SEQ ID NO: 5 (probe 5) are complementary sequences to 5th through 12th, 4th through 11th, and 3rd through 10th bases of the sample DNA, respectively.

The temperature Tm, at which these probes are hybridized with the sample DNA, was measured using the DNA chip according to the present invention.

First, a DNA chip according to the present invention having 36 probe cells, comprising 4 kinds of probes (probe 2 through probe 5) immobilized on 9 probe cells per each probe, is prepared. FIG. 13 is a schematic plan view of a chip. Previously labeled sample is injected onto this chip for hybridization. The temperature for hybridiation is set within the range of 10–50° C. for each column at intervals of 5° C. for the probe cells arranged forming column a through column i as shown in FIG. 13 (10° C. for column a, 15° C., for column b, 20° C. for column c, . . . 45° C. for column h, 50° C. for column i).

Figure 14:
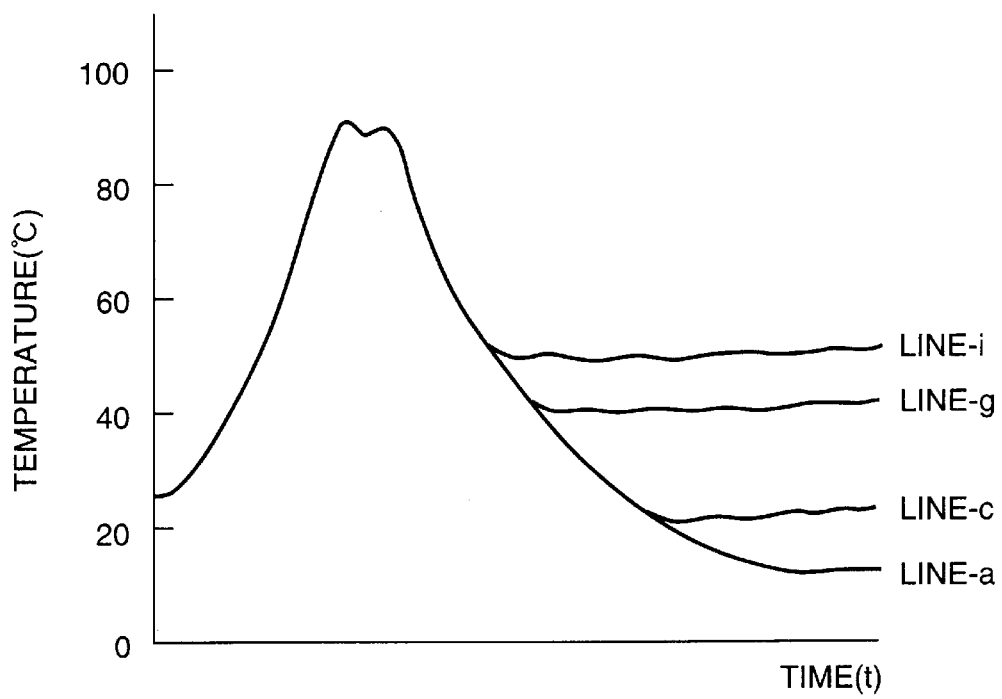
FIG. 14 is a schematic diagram showing the change in temperature of probe cells belonging to column a, column c, column g and column i of DNA chip of FIG. 13.

The steps of reaction is as the following. FIG. 14 is a diagram schematically showing the change in temperatures of the probe cells belonging to the column a, column c, column g and column i. First, the temperature of the incubator is raised to 90° C. Then, the temperature of the incubator is set to 10° C. to allow the individual probe cells fall in temperature. When the temperature of each probe cell falls to about 50° C., the heater for column i is turned on to prevent the temperature from falling further. Similarly, when the predetermined temperature for hybridization is detected, the heater for each column starts to be controlled ON/OFF in order to maintain the temperature. Consequently, the probe cells belonging to each column can maintain the predetermined temperature to effect the hybridization between the sample and probes. After a certain period of time, the DNA chip is washed with a cleansing solution to remove unhybridized sample and others. The result of hybridization is evaluated by scanning the surface of the chip and measuring the amount of fluorescence emission from each probe cell using a laser-fluorescence co-focal-point microscope.

Figure 15:
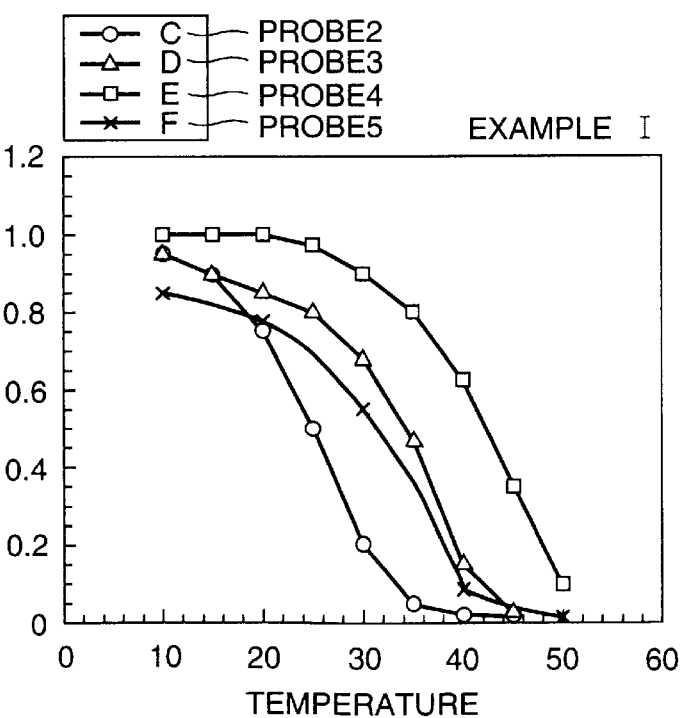
FIG. 15 is a diagram showing the temperature dependency of hybidization in the measurement for the sample DNA of SEQ ID No: 1.

FIG. 15 is a diagram showing the temperature dependency of hybridization in the measurement of the sample DNA. The result is shown with the result of measurement in each column. The maximum amount of emission of light under the condition that the hybridization temperature is 10° C. is standardized as 1. FIG. 15 shows that the amount of hybridization decreases as the temperature rises. Tm is the temperature corresponding to the y-axis value of 0.5. Consequently, the values of Tm hybridization between probes 2 through 5 and sample DNA are found to be 25° C., 34° C., 42° C. and 31° C., respectively. Thus, the chip of the present invention is advantageous in that it enables the hybridization of 4 kinds of probes with the same sample to be carried out under 9 different temperature conditions and the results to be evaluated simultaneously and on comparative basis. The result does not include error from sample preparation, and thus can be obtained with much higher accuracy.

Therefore, when evaluating 1 kind of sample DNA using 8-base probes, the optimal temperature for hybridization varies depending on each probe. It is necessary to select the best probe for evaluating the hybridization characteristics of plural kinds of probes at a time. For this reason, the DNA chip of the present invention, which is capable of evaluating the hybridization temperature characteristics of plural kinds of probes at a time, is quite useful for the evaluation of probes.

With the chip of the present invention, the temperature dependency of hybridization, under the condition where there is a mismatching of one base, can also be evaluated. 2 kinds of DNA fragments given below are prepared.

TGACCGGTAGCAAAATG (SEQ ID NO: 6)
TGACCGGAAGCAAAATG (SEQ ID NO: 7)

Figure 16:
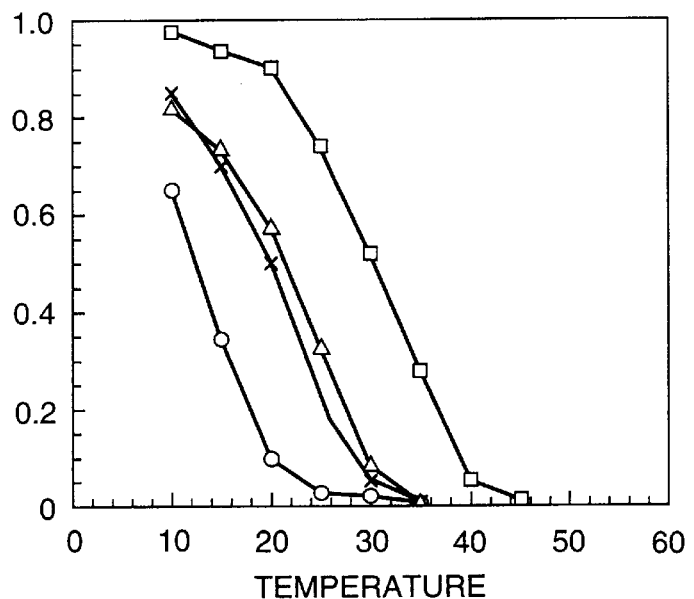
FIG. 16 is a diagram showing the temperature dependency of hybridization in the measurement for the sample DNA of SEQ ID No: 6.
Figure 17:
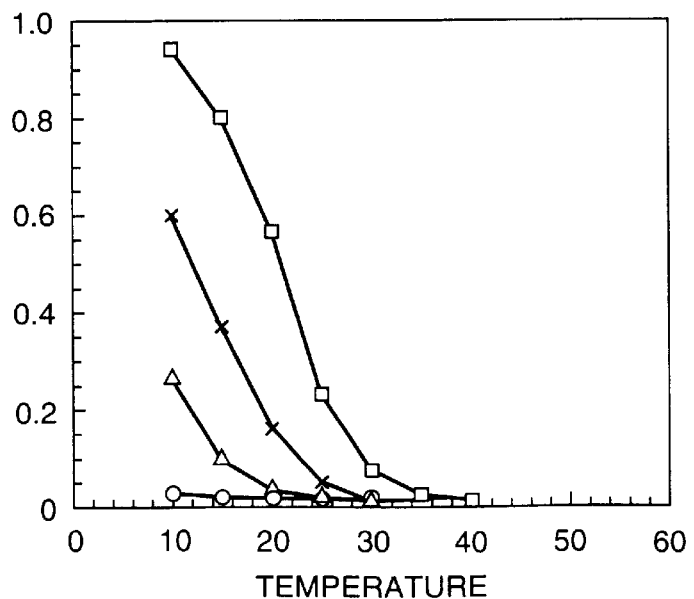
FIG. 17 is a diagram showing the temperature dependency of hybridization in the measurement for the sample DNA of SEQ ID No: 7.

These fragments are examples of 2 kinds of 17-base-length single nucleotide polymorphic DNA fragments differing only the 8th base from 3' end, compared with the SEQ ID NO: 1. For these single nucleotide polymorphic DNA fragments, the temperature dependency is measured using the above chip according to the same procedure as described above. FIG. 16 and FIG. 17 show the results of hybridization using the fragments of SEQ ID NO: 6 and SEQ ID NO: 7 respectively. It is ideal not to occur any hybridizations in such 1-base mismatching. However, as shown in the FIGS. 6 and 7, hybridization actually occurs to a certain extent. In the measurement using the DNA chip, it is generally necessary to discriminate such 1-base mismatching accurately. Accordingly, the evaluation similar to that shown in FIGS. 16 and 17 is carried out to determine the probe to be used and the Tm based on its characteristics. The temperature dependency of the hybridization for each probe can be measured accurately and easily in the present invention.

EFFECT OF THE INVENTION

The present invention provides a biochemical reaction detection chip and its substrate capable of controlling the temperature for the biochemical reaction.

Further, the present invention provides an apparatus and a method for simultaneously carrying out a plurality of biochemical reactions in a plurality of reaction systems with the temperature being controlled for each reaction system, and a storage medium.

All publications, patents and patent applications cited herein are incorporated herein by reference in their entirety.

What is claimed is:

1. A biochemical reaction detection chip, comprising:
a membranous substrate whose heat conductivity is 10 w/mk (watt/(meter·kelvin)) or less;
a plurality of islands provided on one side of said substrate; and
probe cells for immobilizing probes and for detecting the biochemical reaction, said probe cells being provided on the other side of said substrate through a cross section of the substrate and at sites corresponding to the islands,
wherein each of the islands includes a heater for heating said each of the islands, a temperature detector for detecting the temperatures of said each of the islands, a heater terminal for controlling the heating by the heater, and a temperature detection terminal for outputting the result of detection by said temperature detector, and
wherein the heating by the heater is controlled through the heater terminal according to the output of the temperature detection terminal.

2. A biochemical reaction detection chip according to claim 1, wherein said membranous substrate is formed from a kind of material or a composite material selected from a group consisting of silicon nitride, silicon oxide, aluminum oxide and $Ta_2O_5$.

3. A biochemical reaction detection chip according to claim 1, wherein the temperature are controlled separately for each of the islands provided on said substrate.

4. A biochemical reaction detection chip according to claim 1, wherein said heater is composed of an n-type diffused layer, and said temperature detector is formed with a pn junction consisting of a p-type diffused layer and n-type diffused layer.

5. A biochemical reaction detection chip according to claim 1, wherein said probe cell for immobilizing the probe is indented toward said each of the islands.

6. A biochemical reaction detection chip according to claim 1, wherein a p-type diffused layer is provided between said heater and said temperature detector where said substrate is of n-type substrate.

7. A biochemical reaction detection chip, comprising:
a plurality of islands capable of being controlled independently for temperature and provided on intersecting points of a lattice on one side of a membranous substrate;
probe cells for immobilizing probes disposed on the other side of the substrate through a cross section of the substrate; and
probes immobilized respectively on the probe cells,
wherein said probes are arranged according to their Tm values, from highest to lowest, either, from the center of the chip to the outer edge, or from one cross-sectional side of the chip to the opposite cross-sectional side of the chip.

8. A biochemical reaction detection chip according claim 1, wherein the probes are selected from a group consisting of the oligonucleotide DNA probes, oligonuclotide RNA probes and protein probes.

9. A biochemical reaction detection chip according to claim 1, wherein a heat conductor is provided between the islands.

10. A biochemical reaction detection chip according to claim 1, wherein a metal frame is provided on the periphery of said substrate.

11. A method for manufacturing a membranous substrate for biochemical reaction detection chip, comprising the steps of:
a) forming a membrane on one side of the substrate of a heat heater conductor, heat conductivity of said membrane being 10 w/mk (watt/(meter·kelvin)) or less;

b) forming islands on the heat conductor on the other side of the substrate through the cross section of the heat conductor by removing unnecessary portion therefrom; and c) after step b), forming probe cells for immobilizing probes on the membrane.

12. A method according to claim 11, wherein a temperature controller is formed on one side of the flat sheet of the heat conductor and a membrane is formed thereon.

13. A method according to claim 12, wherein a mask having a desired pattern is formed on the side opposite to said membrane, and the islands of the heat conductor corresponding to the masked pattern are formed by etching the masked side until the membrane provided on the opposite side comes to be exposed.

14. A method according to claim 13, wherein said mask is a membrane of silicon nitride.

* * * * *

SEQUENCE LISTING

```
<160> NUMBER OF SEQ ID NOS: 7

<210> SEQ ID NO 1
<211> LENGTH: 17
<212> TYPE: DNA
<213> ORGANISM: Artificial Sequence
<220> FEATURE:
<223> OTHER INFORMATION: sample DNA fragment

<400> SEQUENCE: 1
tgaccggcag caaaatg                                                         17

<210> SEQ ID NO 2
<211> LENGTH: 8
<212> TYPE: DNA
<213> ORGANISM: Artificial Sequence
<220> FEATURE:
<223> OTHER INFORMATION: DNA probe hybridizing with DNA fragment

<400> SEQUENCE: 2 ccgtcgtt                                                                    8

<210> SEQ ID NO 3
<211> LENGTH: 8
<212> TYPE: DNA
<213> ORGANISM: Artificial Sequence
<220> FEATURE:
<223> OTHER INFORMATION: DNA probe hybridizing with DNA fragment

<400> SEQUENCE: 3 gccgtcgt                                                                    8

<210> SEQ ID NO 4
<211> LENGTH: 8
<212> TYPE: DNA
<213> ORGANISM: Artificial Sequence
<220> FEATURE:
<223> OTHER INFORMATION: DNA probe hybridizing with DNA fragment

<400> SEQUENCE: 4 ggccgtcg                                                                    8

<210> SEQ ID NO 5
<211> LENGTH: 8
<212> TYPE: DNA
```

-continued

```
<213> ORGANISM: Artificial Sequence
<220> FEATURE:
<223> OTHER INFORMATION: DNA probe hybridizing with DNA fragment

<400> SEQUENCE: 5 tggccgtc                                                                8

<210> SEQ ID NO 6
<211> LENGTH: 17
<212> TYPE: DNA
<213> ORGANISM: Artificial Sequence
<220> FEATURE:
<223> OTHER INFORMATION: sample DNA fragment

<400> SEQUENCE: 6
tgaccggtag caaaatg                                                     17

<210> SEQ ID NO 7
<211> LENGTH: 17
<212> TYPE: DNA
<213> ORGANISM: Artificial Sequence
<220> FEATURE:
<223> OTHER INFORMATION: sample DNA fragment

<400> SEQUENCE: 7
tgaccggaag caaaatg                                                     17
```